US012011281B2

(12) United States Patent
D'Arcy et al.

(10) Patent No.: US 12,011,281 B2
(45) Date of Patent: Jun. 18, 2024

(54) QUANTIFYING MOTOR FUNCTION USING EEG SIGNALS

(71) Applicant: Health Tech Connex Inc., Surrey (CA)

(72) Inventors: Ryan Clarke Newell D'Arcy, Surrey (CA); Xin Zhang, Surrey (CA); Carlo Menon, Coquitlam (CA); Zachary Frehlick, Surrey (CA); Pamela Tannouri, Surrey (CA)

(73) Assignee: Health Tech Connex Inc., Surrey (CA)

(*) Notice: Subject to any disclaimer, the term of this patent is extended or adjusted under 35 U.S.C. 154(b) by 842 days.

(21) Appl. No.: 17/057,941

(22) PCT Filed: May 24, 2019

(86) PCT No.: PCT/CA2019/000078
§ 371 (c)(1),
(2) Date: Nov. 23, 2020

(87) PCT Pub. No.: WO2019/222833
PCT Pub. Date: Nov. 28, 2019

(65) Prior Publication Data
US 2021/0196182 A1    Jul. 1, 2021

Related U.S. Application Data

(60) Provisional application No. 62/700,416, filed on Jul. 19, 2018, provisional application No. 62/675,866, filed on May 24, 2018.

(51) Int. Cl.
*A61B 5/374* (2021.01)
*A61B 5/00* (2006.01)
(Continued)

(52) U.S. Cl.
CPC .............. *A61B 5/374* (2021.01); *A61B 5/291* (2021.01); *A61B 5/725* (2013.01); *A61B 5/7257* (2013.01);
(Continued)

(58) Field of Classification Search
CPC ......... A61B 5/374; A61B 5/291; A61B 5/725; A61B 5/7257; A61B 5/7264;
(Continued)

(56) References Cited

U.S. PATENT DOCUMENTS

2003/0073920 A1* 4/2003 Smits .................... A61B 5/121
600/544
2005/0113666 A1* 5/2005 Bonmassar .......... A61B 5/0006
600/410

(Continued)

FOREIGN PATENT DOCUMENTS

JP    2010125287 A    6/2010

OTHER PUBLICATIONS

López-Larraz Eduardo et al., Evolution of EEG Motor Rhythms after Spinal Cord Injury: A Longitudinal Study, PLOS One, Jul. 7, 2015, pp. 1-15, vol. 10, No. 7, DOI: 10.1371/journal.pone.0131759, https://journals.plos.org/plosone/article/file?id=10.1371/journal.pone.0131759&type=printable.

(Continued)

*Primary Examiner* — Devin B Henson
*Assistant Examiner* — Matthew Eric Ogles
(74) *Attorney, Agent, or Firm* — McCarthy Tétrault LLP

(57) ABSTRACT

A motor control score is automatically generated for a subject based on electroencephalography (EEG) data represented as a plurality of EEG waveforms obtained from a plurality of EEG electrodes. Each waveform is separated into at least one window, containing a portion of the EEG waveform representative of neural activity corresponding to
(Continued)

a movement performed by the subject. At least one or more frequency components and/or signal components are determined from the EEG data in the window, and a motor control score is determined based on these components. The frequency components may correspond to event-related desynchronization (ERD) response frequency band and event-related synchronization (ERS) response frequency band. In other embodiments, the frequency components correspond to a phase response and the signal components correspond to a signal power spectrum density of the window, which are provided to a primary neural network model to determine the motor control score.

8 Claims, 17 Drawing Sheets

(51) Int. Cl.
  *A61B 5/11* (2006.01)
  *A61B 5/291* (2021.01)
  *G16H 50/30* (2018.01)

(52) U.S. Cl.
  CPC .......... *A61B 5/7264* (2013.01); *G16H 50/30* (2018.01); *A61B 5/1124* (2013.01); *A61B 5/7203* (2013.01)

(58) Field of Classification Search
  CPC ..... A61B 5/1124; A61B 5/7203; A61B 5/369; A61B 5/377; A61B 5/024; A61B 5/16; A61B 5/4064; A61B 5/375; A61B 5/378; A61B 5/38; A61B 5/384; A61B 5/389; A61B 5/388; A61B 5/398; A61B 5/372; A61B 5/37; A61B 5/296; A61B 5/297; A61B 5/31; A61B 5/313; A61B 5/315; A61B 5/726; A61B 5/7267; A61B 5/7271; A61B 5/7275; A61B 5/7282; A61B 5/7285; A61B 5/7289; A61B 5/7292; A61B 5/7296; A61B 5/7235; A61B 5/7239; A61B 5/7242; A61B 5/7246; A61B 5/1126; A61B 5/11; A61B 5/4076; A61B 5/4082; A61B 5/4088; A61B 5/4094; A61B 5/4058; G16H 50/30
  See application file for complete search history.

(56) References Cited

U.S. PATENT DOCUMENTS

| | | | |
|---|---|---|---|
| 2006/0167371 A1* | 7/2006 | Flaherty | G06N 3/061 |
| | | | 600/545 |
| 2013/0138011 A1* | 5/2013 | Ang | A61B 5/375 |
| | | | 600/545 |
| 2013/0237790 A1* | 9/2013 | Riess | A61B 5/291 |
| | | | 600/373 |
| 2013/0245422 A1* | 9/2013 | D'arcy | A61B 5/7246 |
| | | | 600/409 |
| 2015/0148634 A1* | 5/2015 | Garudadri | A61B 5/01 |
| | | | 600/595 |
| 2015/0216468 A1* | 8/2015 | Vidal-Naquet | A61B 5/374 |
| | | | 600/544 |
| 2015/0297106 A1* | 10/2015 | Pasley | A61B 5/741 |
| | | | 600/383 |
| 2017/0164862 A1* | 6/2017 | Dolev | A61B 5/291 |
| 2017/0172497 A1* | 6/2017 | Marquez Chin | A61B 5/7246 |
| 2017/0181915 A1* | 6/2017 | Ang | G06F 3/014 |
| 2019/0166434 A1* | 5/2019 | Petley | H04R 25/505 |

OTHER PUBLICATIONS

Kaiser Vera et al., Relationship Between Electrical Brain Responses to Motor Imagery and Motor Impairment in Stroke, Aug. 14, 2012, pp. 2735-2740, vol. 43, No. 10, ISSN: 0039-2499, DOI: 10.1161/STROKEAHA.112.665489, https://www.ahajournals.org/doi/pdf/10.1161/STROKEAHA.112.665489.

Cheng Dawei et al., Exploring Motor Imagery EEG Patterns for Stroke Patients with Deep Neural Networks, 2018 IEEE International Conference on Acoustics, Speech and Signal Processing (ICASSP), Apr. 15, 2018, pp. 2561-2565, IEEE, DOI: 10.1109/ICASSP.2018.8461525.

Gourab K. et al., Changes in movement-related B-band EEG signals in human spinal cord injury, Clinical Neurophysiology, pp. 2017-2023, vol. 121, No. 12, ISSN: 1388-2457, DOI: 10.1016/J.CLINPH.2010.05.012, Elsevier.

Alazrai, Rami, et al., EEG-based brain-computer interface for decoding motor imagery tasks within the same hand using choi-williams time-frequency distribution, Sensors 17.9 (2017): 1937.

Park, Wanjoo, et al., EEG patterns of subacute stroke patients performing motor tasks correlate with motor functional outcome: Preliminary results, 2016 38th Annual International Conference of the IEEE Engineering in Medicine and Biology Society (EMBC), IEEE, 2016.

* cited by examiner

QUANTIFYING MOTOR FUNCTION USING EEG SIGNALS

TECHNICAL FIELD

The present disclosure relates generally to systems and methods for quantifying motor function using electroencephalography (EEG) measurements. Particular systems and methods disclosed herein may be applied to quantify the motor function of chronic stroke survivors.

RELATED APPLICATIONS

This application claims priority from U.S. application No. 62/675,866 filed May 24, 2018 entitled "Using EEG to Quantify Upper-Extremity Motor Function for Chronic Stroke" and U.S. application No. 62/700,416 filed Jul. 19, 2018 titled "Using Brain Activity to Score Motor Function". This application claims the benefit under 35 USC § 120 of U.S. application No. 62/675,866 filed May 24, 2018 entitled "Using EEG to Quantify Upper-Extremity Motor Function for Chronic Stroke" and U.S. application No. 62/700,416 filed Jul. 19, 2018 titled "Using Brain Activity to Score Motor Function", which are both incorporated herein by reference in their entirety.

BACKGROUND

Assessment of human motor function, both for healthy individuals and individuals impacted by a neurological condition, disease or injury, is relevant for different sectors, including sport, wellness, video gaming, military and clinical applications. For example, stroke is a common condition that impacts motor function, and the ability to accurately and reliably assess stroke recovery can play an important role in the stroke rehabilitation process. Traditionally, clinical assessment of deficit and residual motor function is restricted to bedside examination by a trained clinician. For instance, the Medical Research Council's (MRC) 0-to-5 scale for muscle power assessment, which was originally designed for peripheral neuromuscular disorders, is one of the tools used for clinical motor power assessment. Other standardized semi-quantitative scores, such as the Functional Independence Measurement (FIM), Wolf Motor Function Test (WMFT), and the Fugl-Meyer Motor Assessment (FMMA) are designed for functional assessment and are commonly used in research studies. However, these and other similar scoring systems are neither completely quantitative nor easy to administer. Furthermore, accurate scoring requires both experience and skill from the test administrator, which takes time and effort on the test administrator to acquire.

In view of the foregoing, there is a need to develop improved, automated solutions for consistent and accurate assessments of motor function, Including in cases where motor function has been impacted by a neurological condition, disease or injury.

SUMMARY OF THE DISCLOSURE

In general, the present specification describes a system and method for recording and quantifying EP/ERP waveforms obtained from EEG measurements in a fast, repeatable and automated manner.

One aspect provides a computer-implemented method to automatically generate a motor control score for a subject based on electroencephalography (EEG) data represented as a plurality of EEG waveforms obtained from a plurality of EEG electrodes. The method includes, for each EEG waveform of the plurality of EEG waveforms, separating the EEG waveform into at least one window, wherein each window contains a portion of the EEG waveform representative of neural activity corresponding to a movement performed by the subject; determining, from the EEG data in the at least one window, at least one or more frequency components; and calculating the motor control score based on the at least one or more frequency components.

In a particular embodiment, the one or more frequency components correspond to at least one event-related desynchronization (ERD) response frequency band and at least one event-related synchronization (ERS) response frequency band, and the motor control score is calculated based on at least one ERD and ERS waveform feature extracted from the plurality of EEG waveforms based on the at least one ERD response frequency band and the at least one ERS response frequency band. The at least one ERD and ERS waveform feature can be obtained by: filtering the plurality of EEG waveforms using the at least one ERD response frequency band and the at least one ERS response frequency band; grouping the plurality of EEG electrodes into at least one spatial group, wherein a respective virtual EEG channel is associated with each of the at least one spatial group; generating the ERD and ERS waveforms from the respective virtual EEG channel associated with each of the at least one spatial group; and extracting the at least one ERD and ERS waveform features from the ERD and ERS waveforms associated with each of the at least one spatial group.

The at least one ERD response frequency band and the at least one ERS response frequency band may be determined by: calculating an average window using a set of waveform windows associated with a single EEG electrode; outputting a time-frequency domain representation of the averaged window; identifying, within a first frequency range of the time-frequency domain representation, the at least one ERD response frequency band; and identifying, within a second frequency range of the time-frequency domain representation, the at least one ERS response frequency band.

In another embodiment, the one or more frequency components correspond to at least one phase response of the at least one window, and at least one or more signal components are determined from the EEG data in the at least one window, the one or more signal components corresponding to at least one signal power spectrum density of the at least one window. The motor control score is calculated using a primary neural network, the primary neural network being provided with the EEG data in the at least one window as input comprising at least one phase response and at least one signal power spectrum. The phase response of the EEG data in the at least one window comprises frequency elements within at least the alpha band and the beta band.

The primary neural network can be configured using regression with a training data set having phase responses and power spectrum densities in a plurality of EEG waveforms, and a plurality of manually-assessed clinical motor function scores associated with the plurality of EEG waveforms.

In a particular embodiment, the phase response and the power spectrum density are calculated from a corresponding frequency domain representation of the at least one window. The primary neural network model is configured using a configuration framework comprising at least two two-dimensional convolutional neural network layers, at least two max pooling layers, and at least two fully connected layers.

Additional aspects of the present invention will be apparent in view of the description that follows.

BRIEF DESCRIPTION OF THE DRAWINGS

Features and advantages of the embodiments of the present invention will become apparent from the following detailed description, taken with reference to the appended drawings in which.

DETAILED DESCRIPTION

Figure 1:
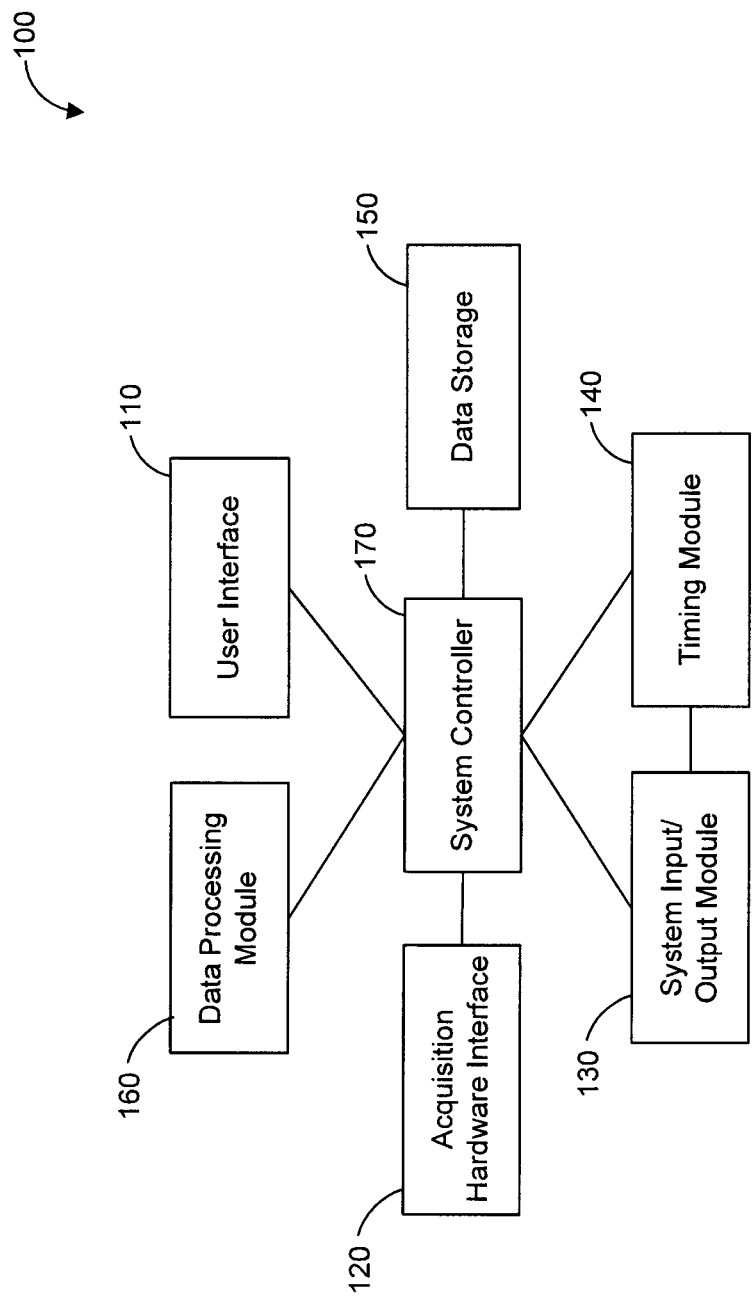
FIG. 1 is a block diagram of a mobility assessment system.

The description that follows, and the embodiments described therein, are provided by way of illustration of examples of particular embodiments of the principles of the present invention. These examples are provided for the purposes of explanation, and not limitation, of those principles and of the invention.

Electroencephalography (EEG) is a non-invasive, electrophysiological method of monitoring brain activity, using multiple electrodes placed on the scalp of a subject to measure voltage fluctuations resulting from ionic current within neurons of the brain. EEG is a tool in neurological practice, with several applications in the management of patients who have suffered or are suffering from a motor function-impacting state associated with the brain. As used herein, "motor function-impacting state" refers to any brain-related injury, condition or disease that affects an individual's motor function. A motor function-impacting state includes, for example, stroke (e.g. ischemic, hemorrhagic, transient ischemic attack, cryptogenic and brain stem stroke), acquired brain injury whether traumatic or non-traumatic, Parkinson's, Alzheimer's, cerebral palsy, and the like. EEG changes during the rehabilitation process can be used to predict motor recovery after suffering a motor function-impacting state. EEG can also be used as a prognosis/assessment tool with results calculated from the EEG signal (for example, delta alpha ratio (DAR), Brain Symmetry Index (BSI), and Large-Scale Phase Synchrony). EEG also has many potential non-clinical applications within sectors such as robotics, entertainment, and wellness, such that certain embodiments of the technology described herein may also be used for healthy individuals to improve their wellness, their sport performance, their alertness during the performance of various tasks where motor performance is relevant.

In the case of stroke, previous EEG work has largely been performed with an acute or sub-acute stroke population. The inventors herein have recognized that EEG biomarkers can be adapted for use in assessing the motor function of chronic stroke survivors as well as survivors of other types of motor function-impacting state. The application of EEG to assess motor function may address drawbacks of existing assessment techniques which (1) often require bedside examination by a trained clinician and/or (2) are neither completely quantitative or easy to administer since accurate scoring relies at least in part on the experience and skill of the test administrator.

Using EEG data to assess motor function may provide a more quantitative assessment and the opportunity to automate the process associated with the determination of a motor control score as described herein. Such methods may also leverage modern computing techniques such as the use of artificial neural network based machine learning methods, which enable the search for additional meaningful features in EEG data. While the exemplary implementations disclosed herein use EEG data, it is to be understood that certain systems and methods disclosed herein may be adapted and applied to any time-varying signal associated with brain activity, such as electrooculography (EOG), magnetoencephalography (MEG) and other types of bioelectric signals, near infrared spectroscopy (NIRS), functional NIRS (fNIRS), functional magnetic resonance imaging (fMRI), and the like.

Disclosed herein is an EEG acquisition and processing system operable as a tool to replace the use of traditional motor function assessments in clinical applications. The disclosed technology may also be used for assessing brain function and motor performance in non-clinical applications such as the wellness and entertainment industries. For illustrative purposes, the examples below are provided in the context of quantifying motor function of stroke survivors and in healthy individuals for comparison. However, it is to be understood that the systems and methods discussed herein are not limited to stroke, and may be adapted and applied to assess motor function of healthy individuals including athletes, seniors, and children, or patients who have experienced other types of a motor function-impacting state, such as, without limitation, acquired brain injury whether traumatic or non-traumatic, Parkinson's, Alzheimer's, and cerebral palsy. The system is intended to automate mobility assessment of individuals so as to improve assessment accuracy over existing clinical motor assessment methods or non-clinical motor performance metrics.

An embodiment of the mobility assessment system described in greater detail below acquires EEG waveforms and automatically identifies features of interest within a desired time period. These features are processed to determine and output a corresponding "motor control score" that is indicative of the patient's motor function. The features of interest in the present disclosure may include event-related desynchronization (ERD) and event-related synchronization (ERS) waveforms and features obtainable from one or more EEG signals.

ERD and ERS (individually and collectively, ERD/ERS) are non-phased locked EEG responses which indicate, respectively, a relative EEG signal power decrease and EEG signal power increase in relation to the timing of a specific neural process. These signals are characterized for both sensory and motor processes (e.g. associated movement such as tapping of fingers). In particular, they are used as indicators of motor activity, with different ERD/ERS characteristics in the movement preparation, movement execution and post-movement phases.

ERD/ERS are understood to be frequency band-limited, such that different EEG bands can simultaneously have different ERD/ERS characteristics. The waveforms are subdivided into frequency bands (e.g. designated as alpha, beta, gamma, theta, delta) based on their signal characteristics; each band is associated with particular behaviour, such as relaxing (alpha), physical activity (beta), stress (gamma), drowsiness (theta) and sleeping (delta). Additionally, ERD/ERS are highly related to the spatial mapping of the brain's cortex. Motor-related ERD/ERS are generally known to occur mostly around the central sulcus where brain structures related to motor-control are located, with the two hemispheres of the brain being differentially affected. EEG can be used to record such ERD/ERS characteristics at multiple brain sites at once.

In the present disclosure, ERD/ERS can be considered to be indicators of a person's ability to control their motor function. During movement, healthy individuals have EEG signal characteristics that are distinguishable from those of individuals with impaired motor control, such as those recovering from stroke. To generate an EEG-based assessment of motor function, an individual wears an EEG device while performing a series of simple benchmark movements (such as finger tapping repeated several times) with time stamping at movement execution. In some embodiments, the EEG device may be operated to capture further brain EEG signals relating to the subject's 1) resting state brain activity (no specific actions being done); 2) imaginary movements (which have similar ERD/ERS properties but no time stamping); and/or 3) physical movements with no time stamps or automatically detected timestamps. ERD/ERS information is then extracted from the raw EEG data to derive a motor control score.

The procedure for assessment of motor function according to one embodiment involves using time-frequency analysis to identify EEG frequency bands containing the desired ERD/ERS characteristics; filtering the EEG channels using the frequency bands identified in the time-frequency analysis; spatially dividing electrodes associated with the EEG channels into electrode groups; optimizing the contributions of the electrodes within each electrode groups; deriving ERD/ERS waveforms for each electrode group in the form of full-time curves of ERD/ERS behaviour before and after movement; extracting features from the before and after movement from the ERD/ERS waveforms; and calculating the motor control scores from the extracted features.

The particulars of the various steps of the procedure are described in greater detail below.

The EEG acquisition and processing system disclosed herein can be used by clinicians, physiotherapists and other healthcare professionals as a tool for assessing motor function at a particular point during rehabilitation after brain injury (e.g. from stroke or from other conditions such as head trauma). The system may further be used to record and track motor function assessment scores of a patient with brain injury over time to evaluate whether the patient's condition is improving, or to inform healthcare professionals whether the rehabilitation program is working or requires adjustment. In certain cases, the system can be used as a tool for monitoring compliance to a rehabilitation program, a tool for prediction of potential for recovery, or a tool for patients to receive feedback (periodically or in real-time) on their rehabilitation exercises.

Referring first to FIG. 1, shown therein is a block diagram of a mobility assessment system 100 operable to acquire and automatically process EEG data to output a corresponding quantitatively-obtained motor control score. In the present embodiment, mobility assessment system 100 interfaces with data acquisition components for acquiring EEG signals from a patient (e.g. human or animal subject), healthy or suffering/recovering from a motor function-impacting state. Mobility assessment system 100 includes data processing components for identifying features of interest from the acquired EEG signals for use as the basis for determining the corresponding motor control score, as described in greater detail below.

In some embodiments, mobility assessment system 100 can be implemented using a general purpose computing device. The general purpose computing device may be configured to communicate with suitable EEG hardware to acquire EEG signals. In particular embodiments, electrooculography (EOG) signals are used in addition to, or instead of, EEG signals. As such, the general purpose computing device may be configured to communicate with suitable EOG hardware to acquire EOG signals. Mobility assessment system 100 can incorporate other sources of data, such as heart rate, light, movement, and the like. The computing device may take various forms, including, but not limited to, desktop computers, laptop computers, cloud-based servers, and mobile computing devices such as tablets, smartphones, and other portable devices. In another embodiment, mobility assessment system 100 can be implemented as a standalone device configured and/or programmed specifically to provide functionalities described herein. A description of the various components of mobility assessment system 100 is now presented.

Mobility assessment system 100 includes a user interface 110 that can be presented as a graphical user interface on a display screen for a user to control the various aspects of an EEG data acquisition or "scan" session and to review the status of mobility assessment system 100. For example, input controls (e.g. on-screen keyboard or physical keyboard) can be provided to allow parameters of the scan session to be entered. Parameters can include contextual information such as the name of the subject, the condition of the subject (e.g. stroke, traumatic brain injury, etc.), the type of movement being tested/recorded (e.g. button tapping, reaching arm, etc.), physical or imaginary movement, the limb being used (e.g. left/right arm), the type of processing algorithm applied to interpret the data, and the location of the scan session.

During a scan, user interface 110 is operable to indicate whether errors have been detected by mobility assessment system 100 that would affect the collection or quality of the scanned data. For example, a scan may not proceed if the EEG hardware is not responsive or where EEG electrode impedance levels are outside of a threshold value or range. After the scan, the user can employ user interface 110 to save scan data and/or scan reports to data storage 150 for retrieval and review at a later time.

Figure 2:
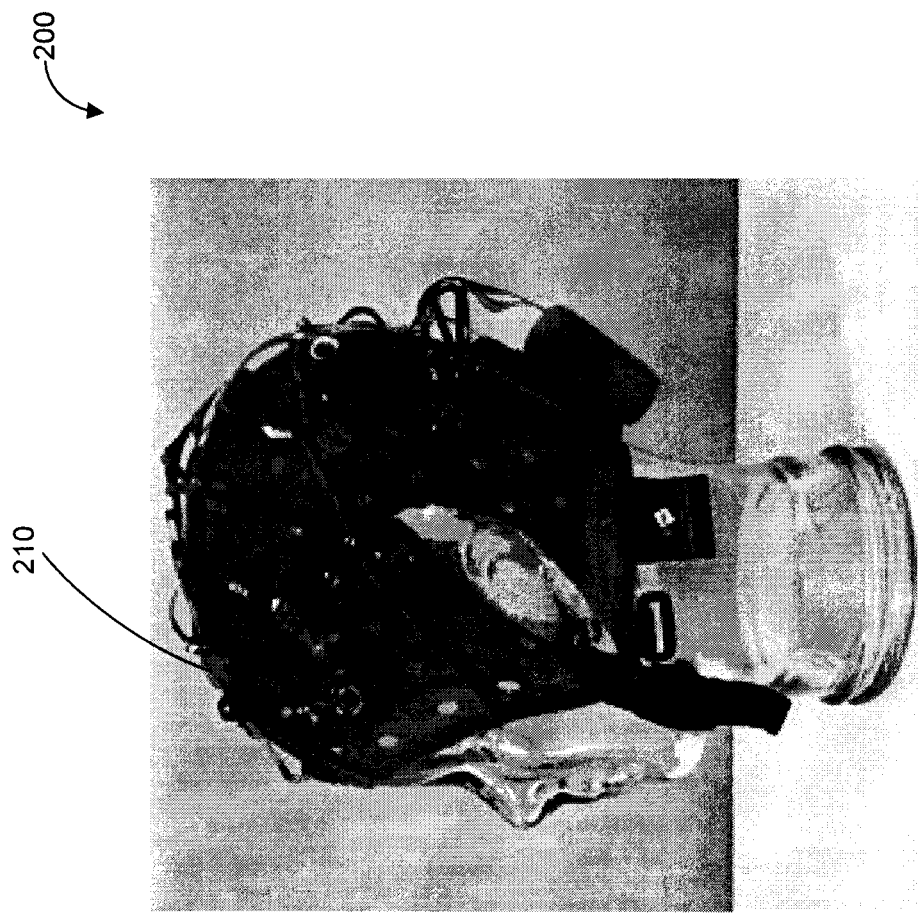
FIG. 2 is an image of EEG acquisition hardware used in conjunction with the mobility assessment system of FIG. 1.

Acquisition hardware interface 120 is operable to establish a communication link between mobility assessment system 100 and EEG acquisition hardware 200, as shown in FIG. 2, for collecting EEG signals from at least one EEG electrode 210. The communication link can be established through any method known to those in the art, including, but not limited to, wired interfaces, wireless interfaces, or a combination of wired and wireless interfaces. The status of the communication link can be indicated in user interface 110 to indicate whether or not the link is active. For example, an indicator in user interface 110 may use a green indicator to show that the link is active and a red indicator to show that the link is inactive.

In some embodiments, acquisition hardware interface 120 further includes an interface for communicating with EOG hardware for the measurement of a subject's ocular activity (e.g. eye movements and blinking) using electrodes placed above and beside the eye socket of the subject. In some embodiments, acquisition hardware interface 120 is operable to scan for available EEG and/or EOG hardware equipment intended for use with mobility assessment system 100 and select the proper communication protocol to establish a communication link therewith.

EEG electrode impedance may affect the quality of the resulting EEG signal, and therefore, may have an impact on the ability to obtain usable ERD/ERS characteristics from the EEG data for analysis. As such, in some embodiments, acquisition hardware interface 120 may also be operable to gather impedance measurements from the EEG hardware. For example, system controller 170 may periodically poll (e.g. on demand or at a pre-determined polling frequency) the EEG hardware via acquisition hardware interface 120 for impedance measurements. The gathered impedance values can be displayed in user interface 110. For example, user interface 110 may graphically indicate electrode impedance using a colour map to indicate impedance quality or display a schematic diagram of electrode locations with impedance indicators.

System input/output module 130 is operable to handle system input and output tasks of mobility assessment system 100. For example, user interface 110 is used to present information and receive data input from a user in which the corresponding inputs entered via the user interface 110 are handled by system input/output module 130 by relaying input data to other modules or performing actions in response to received inputs. Inputs can include user input from an input device such as a switch, button, mouse, keyboard, touch screen, button-based clicker device, EMG sensor, video camera (e.g. to observe and record the movement while it is taking place for time stamping purposes) and the like, or data input from data storage 150. Output can include graphical images for display on a display screen or audio/visual cues/commands for a test subject to carry out certain benchmark movements. For example, an audio cue may be outputted to instruct the test subject to perform a series of simple benchmark movements such as finger tapping, once every self-estimated 10 second. In one implementation, EEG data of healthy subjects were collected by the subject performing the benchmark clicking/tapping movements with the dominant hand. The benchmark clicking/tapping movements can be captured using a hardware button-based clicker device or a muscle electromyography (EMG) sensor. For subjects with chronic stroke, the EEG data were collected by clicking/tapping with the impaired hand. The corresponding EEG data can therefore be recorded, along with suitable timestamp data to indicate the performance of the benchmark movement.

Timing module 140 is operable to control the timing of audio/visual instructions that are outputted during a scan session. The timing module 140 may further be operable to generate the timestamp data noted above. For example, timestamps can correspond to signals generated by one of the above-mentioned devices such as a button-based clicker device, EMG sensor or camera. When a signal (which is indicative of movement) is generated by one of these devices, a corresponding timestamp value may be generated to flag the performance of a movement. In an alternate implementation, the timing module may be configured to generate timestamps for the resting state noted above for the purposes of capturing EEG data when the subject is at rest, performing no action. In this implementation, the subject may be specifically instructed to remain still for a period of time. Upon generating these instructions, a timestamp is also generated to indicate the start of a rest period. The rest period can last for a suitable period of time such as a period in the range of 1-5 seconds, 1-7 seconds, or 1-10 seconds or any other suitable periods of time. The EEG signals corresponding to such rest periods may be considered in the calculation of the motor control scores in conjunction with EEG signals corresponding to movement.

Data storage 150 is operable to store information and data used by mobility assessment system 100 such as configuration files and data files relevant to the determination of motor control scores. Data storage 150 is further operable to store scan session data such as raw and processed EEG and/or EOG data and related reports. Data storage 150 can be implemented in a manner known to those in the art. For example, data storage 150 may be a magnetic or optical disk drive, solid state drive, networked disk drive, distributed storage resource (e.g. cloud-based storage), database, and the like.

Data processing module 160 is operable to process the acquired EEG and/or EOG signals to automatically identify ERD/ERS waveform features of interest and for calculating the corresponding motor control score. As noted above, for feature selection, ERD/ERS characteristics within the EEG data provide indicators of motor function. It is understood that during movement, healthy individuals have EEG signal characteristics that are distinguishable from individuals with impaired motor control, such as those recovering from a stroke.

In some embodiments, data processing module 160 may also be used to provide processing power to other elements of mobility assessment system 100. For example, data processing module 160 can be triggered by system input/output module 130 to synthesize audio and/or visual commands for the test subject.

Figure 3:
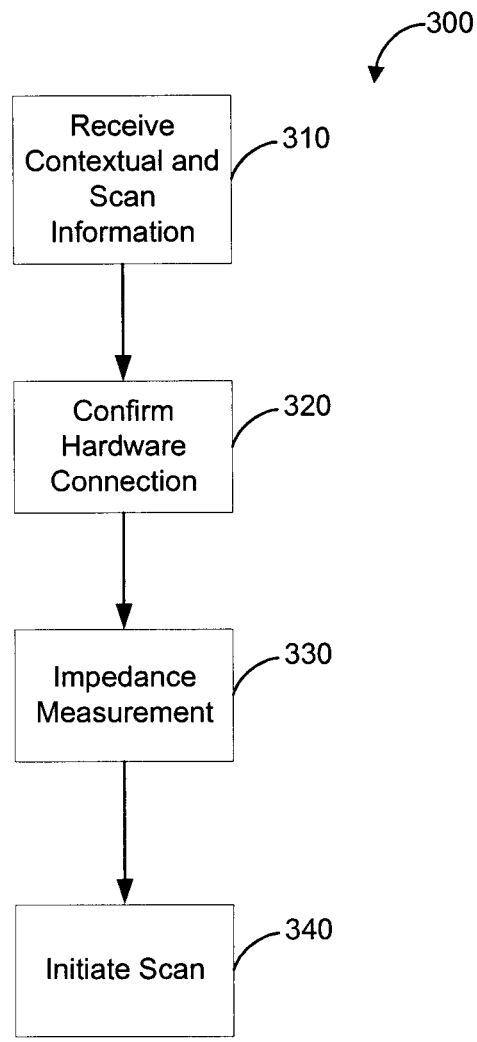
FIG. 3 is a flowchart of a procedure for carrying out an EEG scan using the mobility assessment system of FIG. 1.

System controller 170 is operable to coordinate the operation of mobility assessment system 100, including acquisition of EEG and/or EOG data and processing of such data. FIG. 3 shows a flowchart illustrating a method 300 that may be carried out by system controller 170 to conduct a scan according to one embodiment. In some embodiments, the system controller can be implemented by way of a computerized process that oversees one or more aspects of the operation of mobility assessment system 100 and/or one or more steps of method 300. For example, a computerized process may control the polling frequency of acquisition hardware interface 120 to ensure compliance with electrode impedances (as explained in more detail below). In other embodiments, the system controller 170 may include user input to oversee one or more aspects of the operation of mobility assessment system 100 and/or one or more steps of method 200. For example, the system controller may receive input from a user to open a suitable data processing suite and manually process a data file from data storage 150. In yet other embodiments, user input is required to coordinate the operation of mobility assessment system 100 and/or the steps of method 300.

Referring to FIG. 3, at step 310 of method 300 contextual information (e.g. clinic information and location of the scan) as described previously and scan information (e.g. identifier of the subject, the run number) is received. Such information may be inputted by the user, for example, via user interface 110.

At step 320, an active communication link with the EEG and/or EOG hardware is confirmed. For example, system controller 170 may query acquisition hardware interface 120 of its status. If the status indicates that there is no active connection, or the attempts to connect to the EEG and/or EOG hardware fail, then an error indicator or a message can be generated for display on user interface 110 as described previously. Alternatively, a sound may be generated to alert the user of a connection problem. These alerts would prompt the user to address the connection problem. If an active communication link between the acquisition hardware interface 120 and the acquisition hardware (i.e. the EEG and/or EOG hardware) is present, then method 300 may proceed to step 330.

As noted previously, EEG electrode impedance may affect the quality of the EEG signal, and therefore, it may affect the ability to reliably extract ERD/ERS features from the EEG signal. As such, at step 330, impedance measurements are performed to verify whether the measured impedance values are outside of a threshold value or range. For example, for a particular set of EEG electrodes, impedance values below a certain threshold value are preferred. As such, measurements of impedance may be made and then compared against this threshold value. Impedance measurements can be requested for any EEG electrode position in a given array of electrodes. For example, the Fz, Cz, Pz and/or EOG electrode may be at position hEOG (e.g. "horizontal EOG"—EOG electrode placed beside the subject's eye, near the temple) or vEOG (e.g. "vertical EOG"—EOG electrode placed above the subject's eye). In some embodiments, the EOG and EEG electrodes may be associated with different threshold values. In other embodiments, the EOG and EEG electrodes may be associated with the same threshold value. In some other embodiments, some EEG electrode positions (such as C3, CZ and C4 which are closest to the motor regions of the brain) may have lower impedance thresholds to ensure that these electrodes are prioritized. EEG and EOG electrodes may be positioned as shown in FIG. 2, or may take any suitable spatial location and configuration to record the signals.

If the measured impedance values of the EEG and/or EOG electrodes are satisfactory (e.g. below the threshold) then the next step of method 300 can be performed. However, if the measured impedance values are not satisfactory, then an error indicator or a message can be generated for display on user interface 110. Alternatively, a sound may be generated to alert the user that an impedance issue is present. These alerts would prompt the user to address the impedance issue. For example, electrode impedance can be corrected by doing one or more of the following: applying additional EEG conductive gel to the subject's scalp; re-adjusting the electrode/cap to provide an improved fit; removing excess debris from the subject's hair such as hair gel; abrading the scalp to remove non-conducting skin layers; and cleaning the skin of the scalp with alcohol wipes.

As noted previously, impedance measurements may be scanned repeatedly to ensure that the impedance of each EEG and/or EOG electrode is within a desired range. Accordingly, system controller 170 may periodically poll (e.g. on demand or at a pre-determined polling frequency) the EEG hardware via the acquisition hardware interface 120 for updated impedance values.

At step 340, the scan is initiated. Upon initiation of the scan, an audio or visual prompt may be generated to indicate to the subject that a scan is about to begin and provide the subject with information about the scanning process and instructions on how to perform the one or more benchmark movements during the scan. For example, a short video can be played on a display to show the subject how to perform a particular benchmark movement. Following the initial audio or visual prompt, the scan may begin.

During the scan, system controller 170 can record raw data from the EEG and/or EOG electrodes as well as the presence of trigger signals (e.g. from the button-based clicker, EMG or camera) that indicate the performance of a series of benchmark movements. In some embodiments, multi-channel EEG data is received, each channel corresponding to an electrode in a group of electrodes, each positioned at a suitable spatial location to record a respective EEG signal. For example, such data can correspond to the Fz, Cz, and Pz channels of the EEG hardware of FIG. 2 belonging to electrodes embedded in an EEG headset which reside at nominal electrode sites. In another example, electrodes positioned near to the motor regions of the brain, such as the C3, CZ, and C4 channels may be more commonly used for the purpose of acquiring EEG signals for assessing motor ability. In yet other examples, it may be desirable to deploy multiple electrodes clustered in or around the brain's motor areas. Data received from the PO7 and Oz channels of the EOG hardware may also be received, such channels being connected to adhesive electrodes at the vEOG/hEOG locations.

System controller 170 can mark the onset time of movement commands with a timestamp. This task can be accomplished by generating a trigger signal to the EEG hardware, for instance, via acquisition hardware interface 120 or any other suitable system component. In some embodiments, the trigger signal may be a generated pulse manifested as a voltage output that can be received and captured by the EEG hardware and provided to mobility assessment system 100 along with the EEG data. In other embodiments, the trigger signals may be in the form of trigger codes having different code values. For example, the trigger codes may be hexadecimal values that indicate the start of a scan or that a command to perform a particular benchmark movement is provided. For example, a first code may be used to denote a first command of a series of commands, a second code may be used to denote a second command in the series of commands, and so on.

At the successful conclusion of a scan, system controller 170 can save the acquired EEG and/or EOG data to data storage 150. For example, system controller 170 may save the collected EEG and/or EOG data in its raw form in a file. The raw EEG data file can contain the data of all the channels recorded by the EEG hardware during the scan, including all available EEG electrodes, battery level, sample number, and a trigger channel indicating the time points at which a benchmark movement was performed. The EOG data can be saved in a similar manner.

System controller 170 may also save scan-related metadata in a scan metadata file containing contextual information, scan details, scan date and scan time. As such, in the present embodiment, two output files are generated, comprising one output file for the EEG and/or EOG data and another output file for the metadata. The contents of the two output files may be regarded as the "scan data". In other embodiments, the scan data can be combined into the same data file. The saved scan data may be retrieved subsequently by the user and loaded into data processing module 160 to determine ERD/ERS characteristics used to calculate the corresponding motor control score as described in greater detail below.

In an alternative scanning configuration, the most recently saved scan-related data may be automatically loaded into data processing module 160 for processing and analysis. In another scanning configuration, the scan acquisition and signal processing may be conducted in "real-time" concurrently or substantially concurrently. For example, as a scan session is in progress, acquired EEG and/or EOG data can be saved to data storage 150 and also "streamed" to the data processing module 160 for real-time calculation of motor control score.

EEG Data Processing and Optimization

Figure 4:
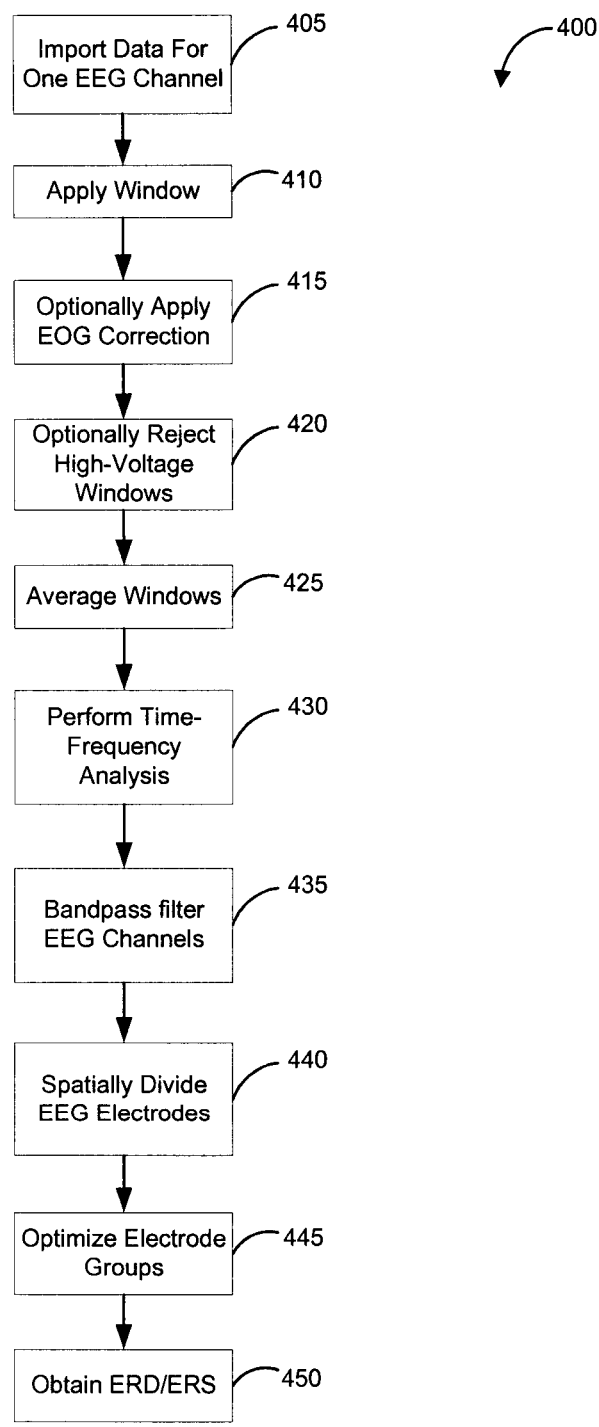
FIG. 4 is a flowchart of a method for processing EEG scan data using the procedure of FIG. 3.

Referring now to FIG. 4, shown therein is a flowchart illustrating a method 400 for processing raw EEG scan data of a given subject using time-frequency analysis to identify the particular frequency components, namely, frequency bands containing the ERD/ERS behaviour and extract the ERD/ERS waveforms. ERD/ERS are known to occur in general frequency bands and at general time periods relative to movement, but precise frequency bands and time periods vary between individuals. In some implementations the frequency band of interest can range between 1 Hz to 45 Hz. In other implementations, the ranges are narrower. For example, the EEG alpha band is generally considered to be in the 8 Hz to 12 Hz range, but varies between individuals, and as a result alpha ERD may occur in only a subsection within this frequency band (such as a 2 Hz width sub-band). Similarly, the EEG beta band is generally considered to be in the range of 13 to 30 Hz, but given variation between individuals the beta ERD may occur in only a subsection within this frequency band (such as a 4 Hz width sub-band).

To determine the frequency bands of interest, data from a single EEG electrode or combination of EEG electrodes that is most likely to contain motor information (generally C3 or C4, which are positioned directly over the motor cortex in each brain hemisphere, or C3/C4 with Laplacian combination of surrounding electrodes) can be used to identify the individual-specific frequency bands. Upon determining the frequencies, ERD/ERS information captured from all of the EEG electrodes used to scan the individual can be extracted for the calculation of motor control scores.

Method 400 may be carried out by the above-described mobility assessment system 100 (wherein the data processing steps of the method may be implemented by data processing module 160), a distributed processing resource such as cloud-based computing clusters, or by way of a separate and/or dedicated digital signal processor implemented using techniques known to those in the art, such as, using an application specific integrated circuit (ASIC) or a field programmable gate array (FPGA).

At step 405 of method 400, EEG data for the desired scan is imported for analysis. As noted above, the EEG data can be recorded when the participants are performing a series of simple benchmark movements (such as finger tapping) with time stamping at movement execution, once every self-estimated 10 seconds. For the healthy participants, the EEG data can be collected by clicking with a button-based clicker device with the dominant hand. For the participants with chronic stroke, the EEG data can be collected by clicking the button-based clicker device with the impaired hand. In some cases, clinical assessments, such as Fugl Meyer Assessment (FMA) and Box and Block Test (BBT), may also be performed to collect clinical assessment scores of motor function from all the participants. Where available, such clinical assessment scores can be provided to the mobility assessment system 100 as additional contextual information. However, such clinical assessment scores are not necessary, as the methods described herein for obtaining motor control scores from EEG information are intended to act as a replacement for the clinical assessments.

In some embodiments, the scan data corresponding to a completed scan may be retrieved from data storage 150. In this case, user interface 110 is operable to provide a list of data files available for processing (e.g. such data files would not have been marked as having been processed). In some other embodiments, user interface 110 may also provide a suitable presentation that concurrently shows data files that have been processed. In yet other embodiments, user interface 110 may periodically scan data storage 150 to identify new data files that have been added so as to facilitate updating of the list of data files that have not yet been processed.

The processed data files may be saved in a format that is different from unprocessed data files. For example, raw EEG data (unprocessed) may be in a human readable format (e.g. CSV format). Processed EEG data files may be in a format that is only machine readable (e.g. using binary file formats such as compressible or compressed file formats that can reduce memory use). In some cases, raw and processed EEG data files may contain information that needs to be kept confidential. As such, raw and processed EEG data files may be encrypted for the purpose of protecting the subject's privacy.

Upon manually or automatically selecting the desired data file for processing, the EEG and/or EOG data and corresponding metadata are "read in" by mobility assessment system 100. In some embodiments, the scan data may be verified to assess its validity prior to processing. For example, an error message may be generated if it is determined that the selected data file is corrupted (e.g. missing certain file parameters such as the indication of the number of samples, incorrect file length, and the like), missing from data storage 150, or has already been processed.

At step 410, the imported EEG data is split into one or more individual windows around the movement timestamps (or rest period time stamps). In one embodiment, the specific time ranges of interest around the movement time point are from −2 seconds to 0 seconds relative to movement for alpha ERD, and from 0 seconds to +2 seconds relative to movement for beta ERS. As noted above, the trigger signals can be used as a timing reference. The sizes of the windows may be chosen according to the expected duration of neural activity related to the movement being performed. For simple tasks such as finger tapping, ERD may begin up to 2-3 seconds before the physical movement, indicating motor preparation. After the movement, ERS may occur for up to 2-3 seconds, indicating a refractory or 'resetting' period. The chosen window size may include all or part of the expected activity duration. A baseline period (where no movement is occurring and the brain's motor activation is in an idle state), defined to be either prior to ERD or after ERS, may also be included in the window to permit calculation of an increase or decrease in neural activity relative to a 'normal'.

In some implementations, prior to applying windowing in step 410, the scan data can be optionally further filtered to remove higher frequency noise, exclude brain frequencies that are not expected to contribute to ERD/ERS, and/or remove low frequency "drift" from the EEG. The filter selected may be any filter suitable for filtering scan data received from the EEG hardware being used. For example, low-pass filters, neural network filters (e.g. autoencoders), and moving average filters can be used. In some embodiments, a bandpass filter having a desired pass band may be applied to the raw data of the EEG and/or EOG channels. For instance, the lower-frequency portion of the pass band is operable to remove the higher frequency noise components while the high frequency portion of the pass band is operable to remove the "drift". In some embodiments, the bandpass filter can be implemented using a minimum passband ripple filter such as a Butterworth filter.

Figure 5A:
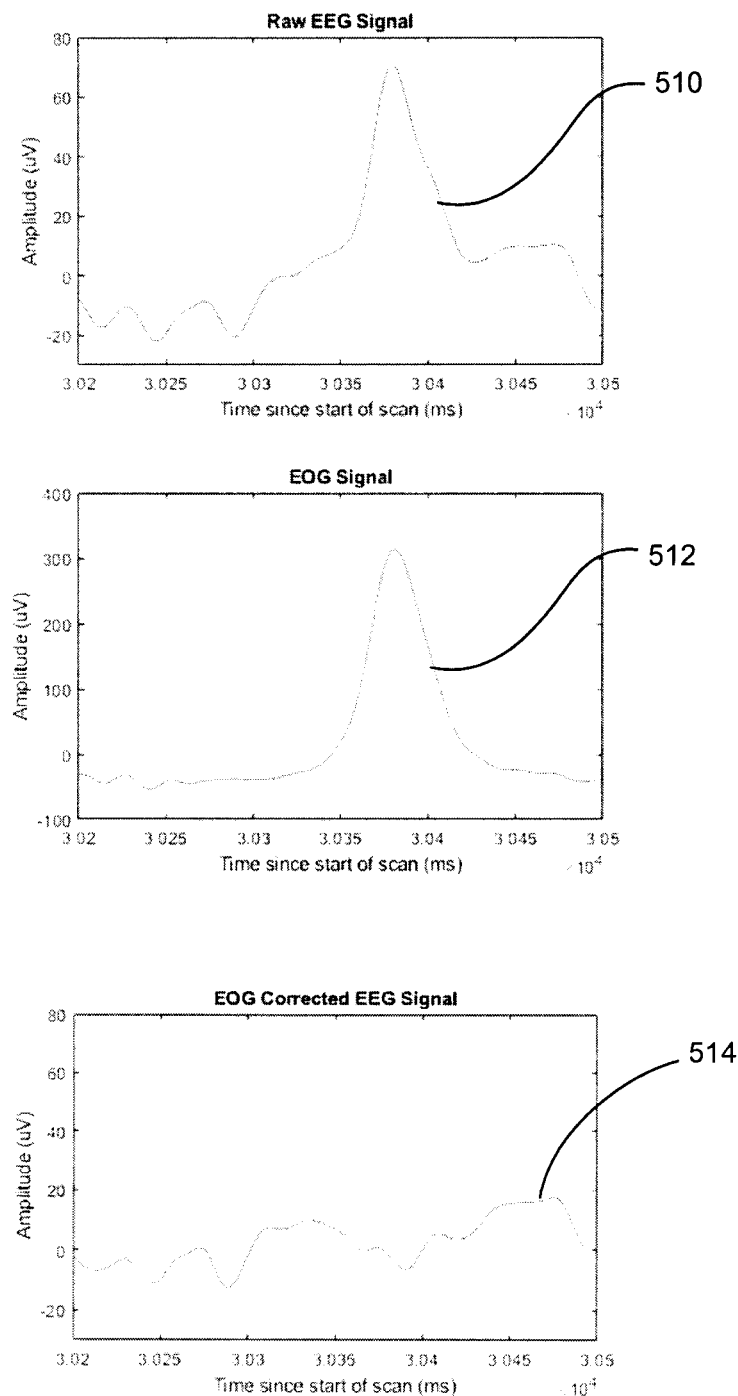
FIG. 5A is a graph of uncorrected and electro-oculogram (EOG)-corrected EEG waveforms and a corresponding EOG waveform used for EOG correction.

Optionally, at step 415, EOG correction is applied by using EOG data from the EOG hardware to remove artifacts resulting from ocular activity detected during the scan such as eye movement and blinking. Specifically, EOG data can be used as a reference as data from the EEG channels is filtered using an adaptive filter. For example, a recursive least squares filter with a kernel size of 5 and Forgetting Factor of 0.9999 can be applied. FIG. 5A shows graphs of the EOG signal 512 indicating eye blink, the resulting "contaminated" EEG signal 510 (Fz channel) containing a corresponding blink artifact, and the corrected EEG signal 514 with a reduced artifact. In other embodiments, any other suitable filter can be used including those that incorporate independent component analysis techniques (ICA) and/or autoregressive moving-average (exogenous) models (AR-MAX). It some cases, it may also be appropriate to optionally reject a part of a window (e.g. where an artefact such as a high voltage is present) and keep another part of the same window. Rejecting data segments with high voltages (or other types of artefacts) could therefore be performed before either windowing (step 410), after windowing or both.

Optionally, at step 420, the EOG-corrected EEG data can be further filtered to remove samples having voltages that exceed a given threshold value. Rejected windows would be excluded from further processing. High voltages may be attributed to various factors including the EEG hardware being used, or environmental factors such as contact of the electrodes to the subject and the degree of movement of the subject. It will be appreciated by a person of skill in the art that the thresholds may take on different values depending on the configuration of the EEG hardware and the subject being scanned. The threshold for a particular system can therefore be determined by way of calibration or using other suitable methods known to those in the art.

At step 425, the windows are averaged together. Averaging several windows allows for the reduction of noise by a factor of $1/\sqrt{n}$, where n is the number of repetitions. Such averaging produces EEG waveforms that are statistically meaningful as compared to individual EEGs that are contaminated by noise. In some embodiments, this averaging can be conducted on a per-channel basis.

Figure 5B:
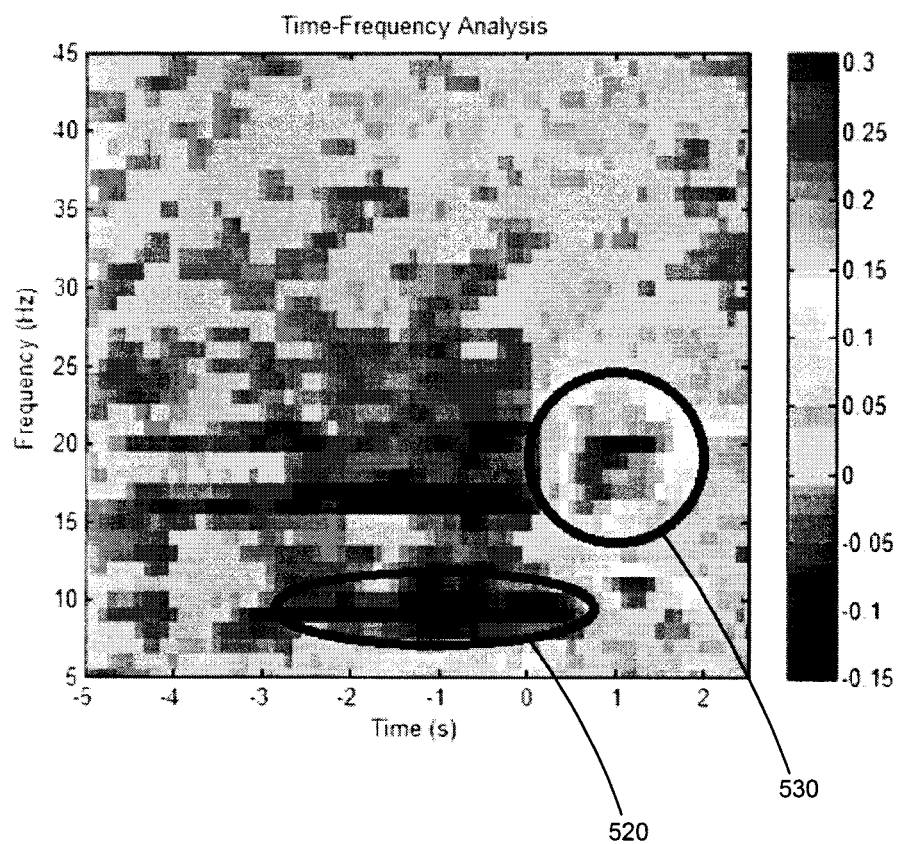
FIG. 5B is a time-frequency map of an EEG signal obtainable from the method of FIG. 4.
Figure 5C:
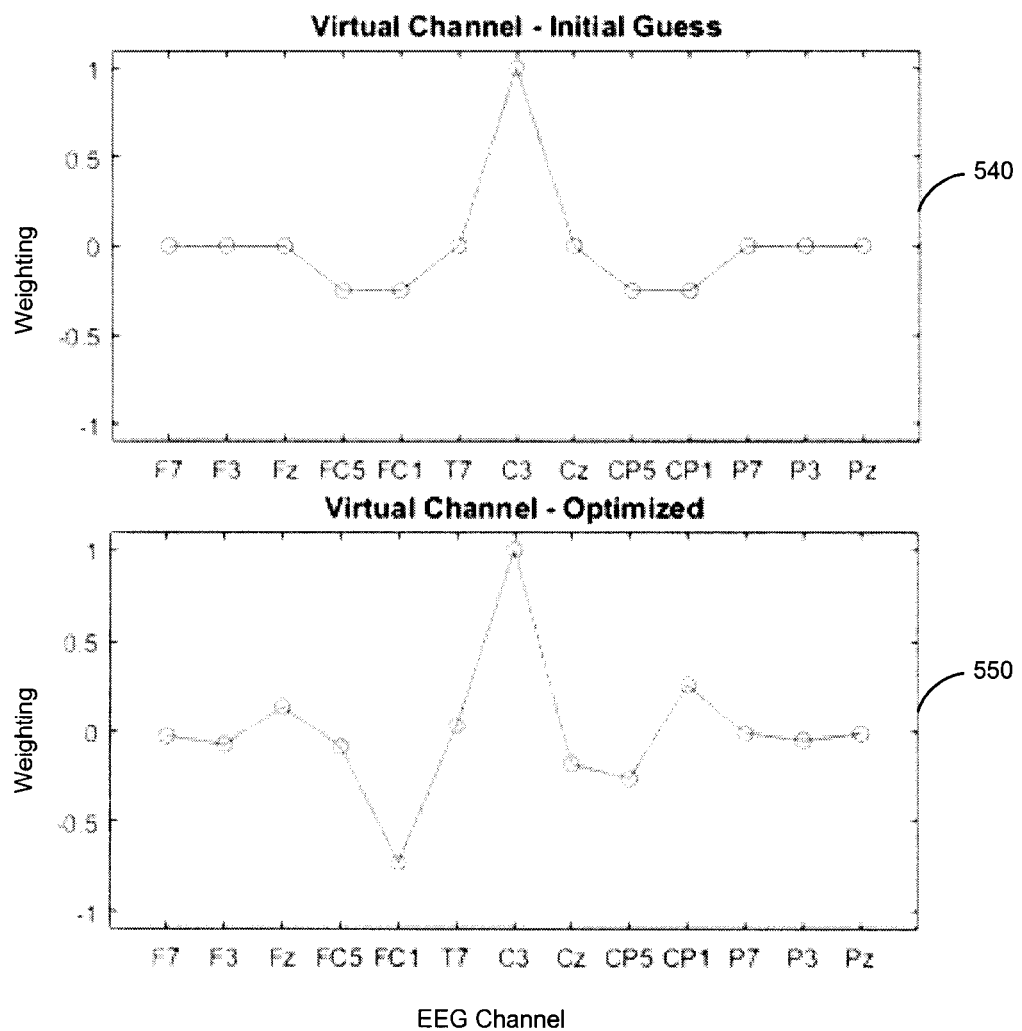

At step 430, after averaging, time frequency analysis is performed on the averaged EEG data to generate a time-frequency map as shown in FIG. 5B. The averaged EEG data can be transformed into the time-frequency domain using techniques known to those in the art. For example, the transformation can be performed by way of using a continuous or discrete Fourier transform or wavelet transform, or fast Fourier transform. For wavelet transforms, a suitable wavelet type may be applied to perform the transformation. For example, wavelets from one or more different families can be used, including, but not limited to, Haar wavelets, Daubechies wavelets, Biothogonal wavelets, Coiflets wavelets, Morlet wavelets, Symlets wavelets, Mexican Hat wavelets, Meyer wavelets, other real wavelets, complex wavelets, and the like.

Within the time-frequency domain, frequency bands are identified within the general frequency ranges noted above based on the generated time-frequency map to locate expected alpha/beta ERD/ERS characteristics. As noted above, ERD/ERS are known to occur within general frequency bands and at general time periods relative to movement. The specific frequency bands, however, typically vary from one individual to another. For example, the EEG alpha band is generally considered to be in the 8 Hz to 12 Hz range, and the beta band is generally in the 13 Hz to 30 Hz range, in which specific frequency bands of different individuals vary within these ranges. Within the general frequency band windows (i.e. 8-12 Hz for alpha, 13-30 Hz for beta) and at specific time points (e.g. from −2 seconds to 0 seconds relative to movement for alpha ERD, from 0 seconds to +2 seconds relative to movement for beta ERS), the frequency bands that best represent the ERD/ERS characteristics for each individual can be automatically identified based on the position within the time-frequency map at which the alpha/beta ERD/ERS characteristics is expected. In one embodiment, a 2 Hz width sub-band within the alpha band and 4 Hz width sub-band within the beta band are considered within the frequency ranges. Other suitable bandwidths of sub-bands may also be used.

In the example time-frequency map of the EEG of one subject shown in FIG. 5B, the regions of interest are represented by an oval marker 520 representing a low signal intensity region corresponding to alpha ERD occurring prior to movement (time 0). A circle marker 530 indicates a region of high signal intensity representing beta ERS after movement. Note that, for this particular case, the highlighted ERD band is from approximately 9 to 13 Hz and highlighted ERS is from approximately 16 to 23 Hz. Sub-bands that are 2 Hz and 4 Hz in width, respectively, can be chosen from these general bands to isolate the frequencies with most prominent ERD/ERS. In some cases, there can be two ERD bands and two ERS bands, or combinations of multiple ERD and ERS bands. Accordingly, the ERD and ERS frequency bands can be located within one or more frequency ranges within the time-frequency map. While a typical case would be an alpha ERD and a beta ERS, there could also be, for example, an alpha ERS, a beta ERD and a gamma ERS (each having a different band). In other embodiments, only one frequency band is used, and both the ERS and ERD are derived from that band.

In one implementation, bands with the lowest average power during the ERD window and highest average power during ERS window are considered. According to one example, for the alpha band an optimal individual band is chosen as a 2 Hz width sub-band, and for the beta band an optimal individual band is chosen as a 4 Hz width sub-band. Increasing sub-band bandwidth as frequency increases is consistent with the uncertainty principle of time-frequency analysis, where frequency resolution decreases at higher frequencies. For example, bandwidth of the sub-band can be proportionally increased with an increase to the frequency ranges of interest. If a higher frequency band is considered, such as the gamma band of 30 Hz to 100 Hz, the bandwidth of the individual band (i.e. the sub-band) should be proportionally wider.

At step 435, the identified frequency bands containing the ERD/ERS characteristics are used to configure suitable filters to filter the EEG data from all of the EEG electrodes. The bandpass filters are then applied to all of the EEG channels and all EEG time samples. After filtering, the filtered data is epoched (e.g. windowed) again using the same time windows applied in step 410.

At step 440, after bandpass filtering, the various EEG channels are spatially divided into one or more spatial groups according to the electrode location and optimized to obtain an overall EEG waveform for each electrode group, as described in greater detail below. For example, if the brain hemispheres are expected to have different signal properties, then the electrodes can be separated into two groups based on their position on the left or right hemisphere. Each electrode within an electrode group is expected to detect the same or similar ERD/ERS characteristics. The rationale for grouping of electrodes in this manner is that while synchronization of brain activity in the two hemispheres is complex, various types of motor activity affect the hemispheres differently. In general, alpha motor activity often occurs in both hemispheres simultaneously and beta motor activity occurs only in the hemisphere contralateral to movement. For individuals with stroke or other brain injury, this pattern may be disrupted.

At step 445, optimization of each spatial group is performed. For each electrode group identified in the previous step, it is assumed that there is an optimal combination of electrodes (e.g. the entire group of electrodes or a subset of the group) that can best provide an EEG representation of the motor processes taking place for the given individual. Specifically, as per the principles of EEG volume conduction, it is generally expected that motor activity will be detectable by more than one EEG electrode and therefore be present in more than one EEG channel. Other brain signals occurring at the same time as motor activity, such as alpha activity from occipital brain areas which indicates fluctuation in attention, will also be detectable by multiple electrodes. Combining these channels would therefore help maximize the quality of output information to improve ERD/ERS detection such that meaningful signals from the motor cortex are optimally detected and other signals (noise, unrelated alpha activity, etc.) are optimally rejected. The brain is a complex organ with multiple types of brain activity ongoing simultaneously in different regions and at different oscillating frequencies. Such activities include motor activity from the central regions, visual activity from the occipital areas, cognitive activity from the frontal regions, and noise. Volume conduction of electrical activity means that all electrodes record all activity types. Therefore, when a group of EEG electrodes records several types of brain activity simultaneously, it may be desirable to apply an optimization technique to retain only the desired type of activity (e.g. motor) and remove all the others. This optimization functions in a similar way as independent component analysis (ICA), where independent sources (e.g. separate types of activities of the brain) can be reconstructed from multiple recordings (e.g. electrodes). The combination of EEG channels that optimizes the capture of one type of brain activity (e.g. motor activity) may depend on each individual subject, as brain structure and motor cortex structure exhibit some variation between individuals. Furthermore, brain injuries such as stroke are known to create unique changes in each affected brain.

The determination of an optimal combination of EEG channels can be automated using various computer-implemented optimization techniques. For example, in one embodiment, gradient descent is chosen to identify the optimal electrode combination. In one application of the gradient descent method, two time windows are chosen for optimization in relation to each other. In one case, ERD is expected to occur before and during the subject's movement. Based on this expectation, a baseline period (e.g. ranging from −5 seconds to −4 seconds before the movement timestamp) and an ERD period (e.g. ranging from −1 second to 0 seconds before the movement timestamp) can be established in this application. For ERS, which is expected to occur after movement, the same baseline period can be used in combination with the post-movement period (e.g. ranging from 0 seconds to +1 second). Alternatively, pre-movement and post-movement periods might be optimized against each other. Widths of selected periods may vary generally within a range of 0.5 seconds to 3 seconds, with a trade-off between increased time resolution and increased vulnerability to noise as width decreases.

Gradient descent can then be performed to carry out optimizations in terms of the ratio between EEG signal power during baseline period and EEG signal power during the ERD period. The objective of this optimization is to identify a combination of electrodes within each electrode group which maximizes the relative difference in signal power. This optimization is expected to result in identification of a combination of electrodes with the lowest possible ERD during movement or highest possible ERS post-movement. Because optimization is calculated as an average across a period, it has the additional benefit of automatically smoothing the output waveform.

At the start of the optimization procedure, an initial guess of a possible electrode combination is provided by assigning each EEG channel a corresponding weighting value (e.g. a weighting of zero means the channel is excluded). This guess may be the same or different from the best guess weighting used in the time-frequency analysis step noted above. From this initial guess, a multi-dimensional gradient curve can be calculated using techniques known to those skilled in the art to identify the incremental weighting changes that will optimize the signal power ratio.

Best guess weighting can be updated with incremental weighting changes. The weighting adjustments can be repeated iteratively until the EEG signal power ratio (the relative power difference between "signal" period and "noise" period) becomes stable. This process is determinative (i.e. an initial channel weight guess will always yield the same 'optimized' output channel weights), but is dependent on the initial guess. Therefore, in some embodiments, multiple initial guesses (either within minor variations or major differences) may be attempted to find an ultimate optimization.

For each frequency band and each electrode group, the optimized channel weights from the optimization procedure is used to calculate a resultant "virtual channel" that best represents the EEG signal in that frequency band/area associated with the electrode group. FIG. 5B shows an example virtual channel weighting plot for channel weights before gradient descent optimization. The initial guess shown in plot 540 is a simple spatial Laplacian filter centered at electrode C3. Plot 550 shows the weightings after optimization. Note that the overall combination of weights remains similar after optimization (with C3 weighted most heavily in this case), but the contributions of surrounding electrodes have adapted. The overall adaptation occurs through an iterative process of incremental changes noted above.

At step 450, each virtual channel is converted into an ERD/ERS power signal by squaring the EEG signal represented by the virtual channel, windowing around each movement trial, averaging over all trials, and normalizing the average to the power signal at a baseline period before the movement. The derived ERD/ERS power signal is then represented as a percentage of the power change with respect to baseline power level. It is noted that existing methods generally apply the squaring of the EEG signal of the EEG channels rather than the virtual channel, without prior application of the gradient descent optimization. Doing so may result in a derived ERD/ERS power signal that may be adequately "clean" (because of various noise sources) for automated motor control score determination using ERD/ERS features.

Calculation of Motor Control Scores

Figure 6:
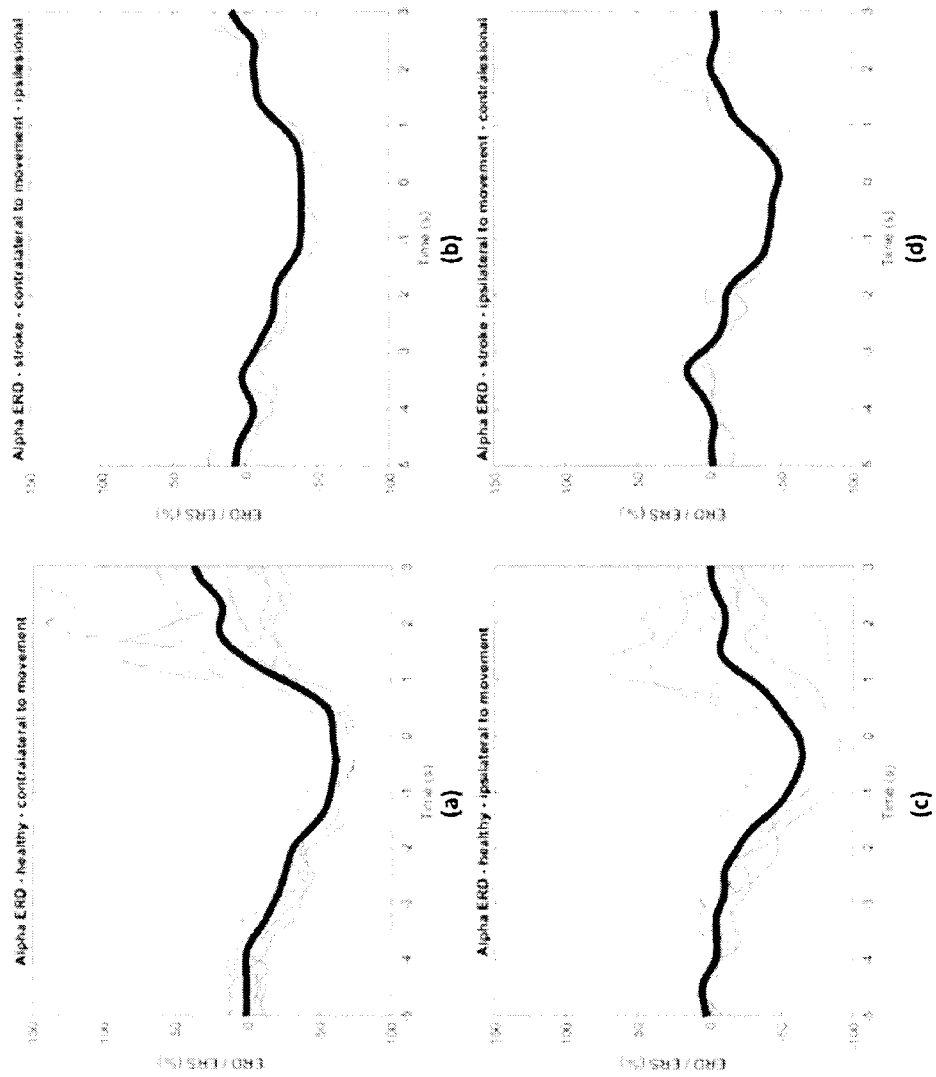
FIG. 6 contains graphs of continuous-time alpha event-related desynchronization (ERD) waveforms for sample healthy individuals and stroke sufferers.
Figure 7:
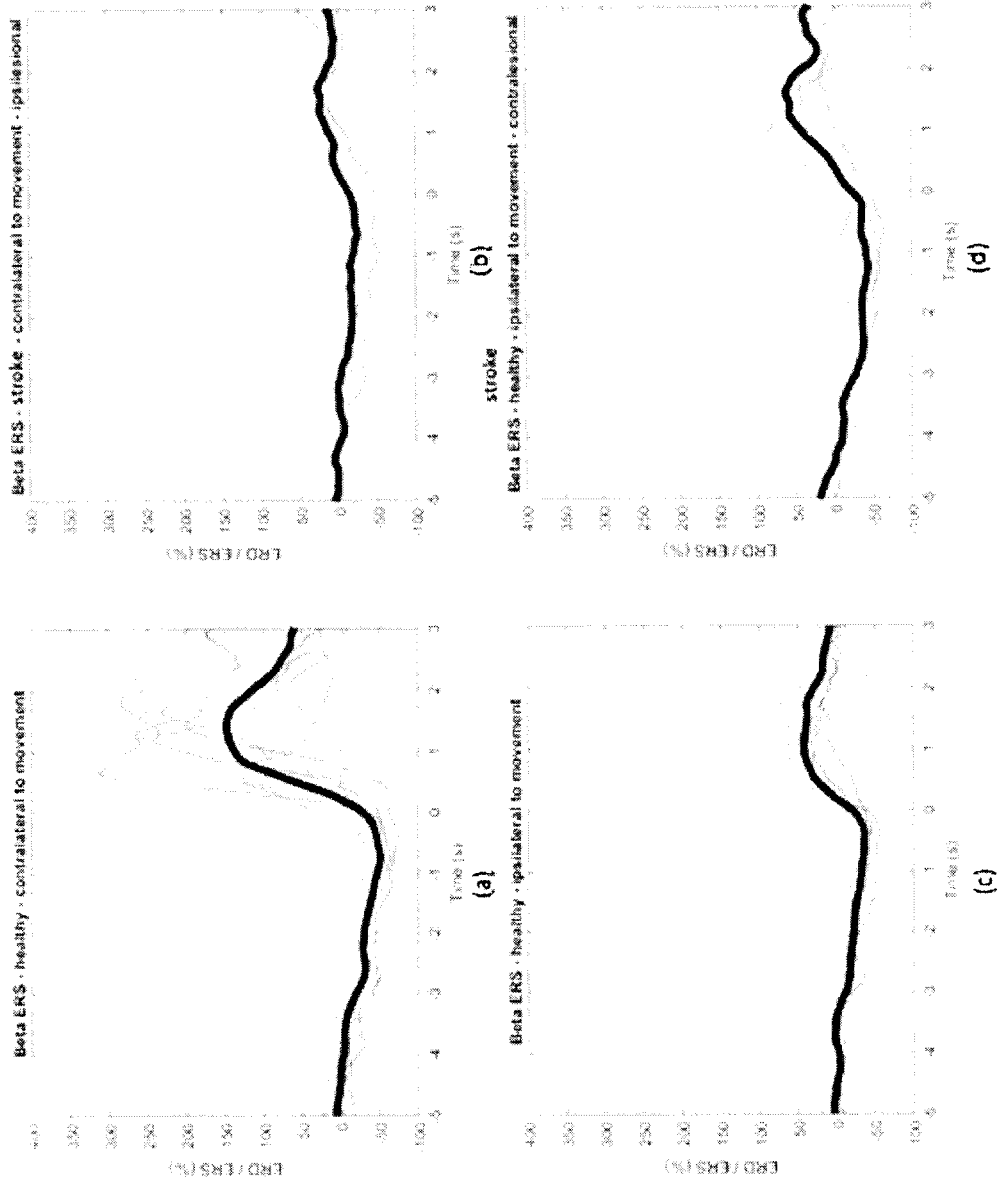
FIG. 7 contains graphs of continuous-time beta event-related synchronization (ERS) waveforms for a sample of healthy individuals and stroke sufferers.

The foregoing procedure produces continuous-time curves of ERD/ERS behaviour before and after movement. Example graphs of alpha ERD and beta ERS signals are shown in FIG. 6 and FIG. 7, respectively for a sample of healthy individuals (graphs (a) and (c) for contralateral to movement and ipsilateral to movement, respectively) and a stroke sufferer (graphs (b) and (d) for contralateral to movement and ipsilateral to movement, respectively). In each graph, the fine lines correspond to the ERD or ERS (as the case may be) signal for an individual, while the bold line represents the averaged ERD or ERS (as the case may be) of the corresponding individual signals.

One or more features can then be extracted from the ERD/ERS curves, such as maximum value and minimum values, time of occurrence of the maximum and minimum, area under the curve, etc. FIGS. 6 and 7 indicate ERD/ERS activity in both frequency bands. While the ERD/ERS curves shown in FIGS. 6 and 7 are time-domain graphs, they contain frequency band information because the above-described bandpass filtering steps have limited the EEG frequency content into narrow bands. Accordingly, the graphs represent activity variations in time for one specific EEG frequency band. For instance, the alpha ERD graphs represent how activity in the 2 Hz wide alpha band varies in time relative to the timestamp of the finger movement. From each of FIGS. 6 and 7, it is generally observable that healthy participants (graphs (a) and (c)) have higher peak values in both ERD/ERS, while the corresponding ERD/ERS signals are relatively "flatter" for participants with chronic stroke (graphs (b) and (d)).

The motor control score can be calculated as a combination of secondary feature values obtainable from the extracted ERD/ERS waveform. The motor control score can then be validated by correlation with clinical motor function assessments, such as Box and Block Test, FMA or WMFT. These clinical assessments may be obtained from the subject on the same day as the scan.

Figure 8:
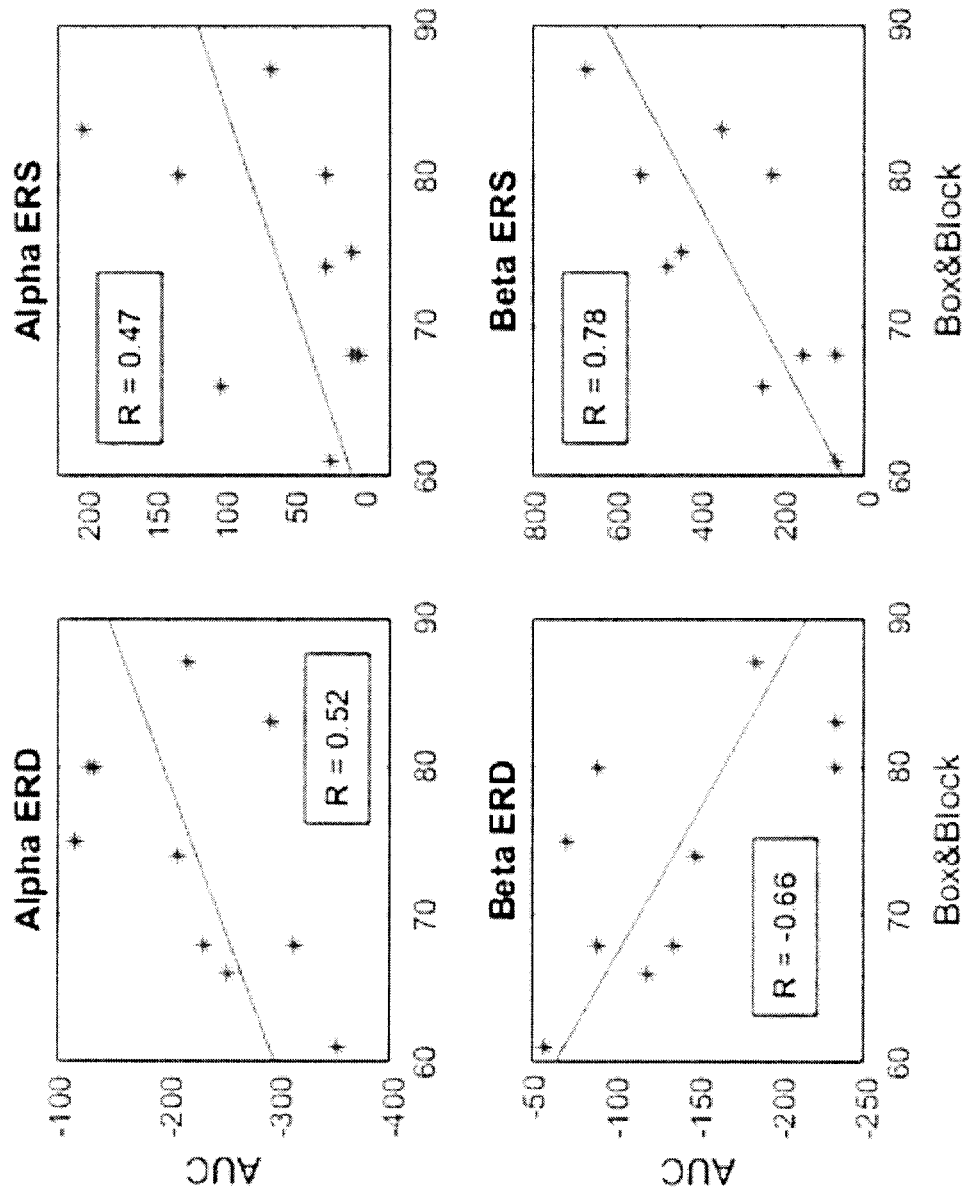
FIG. 8 contains graphs of correlation between an area under the curve of ERD and ERS waveforms and clinical box and block test scores.
Figure 9:
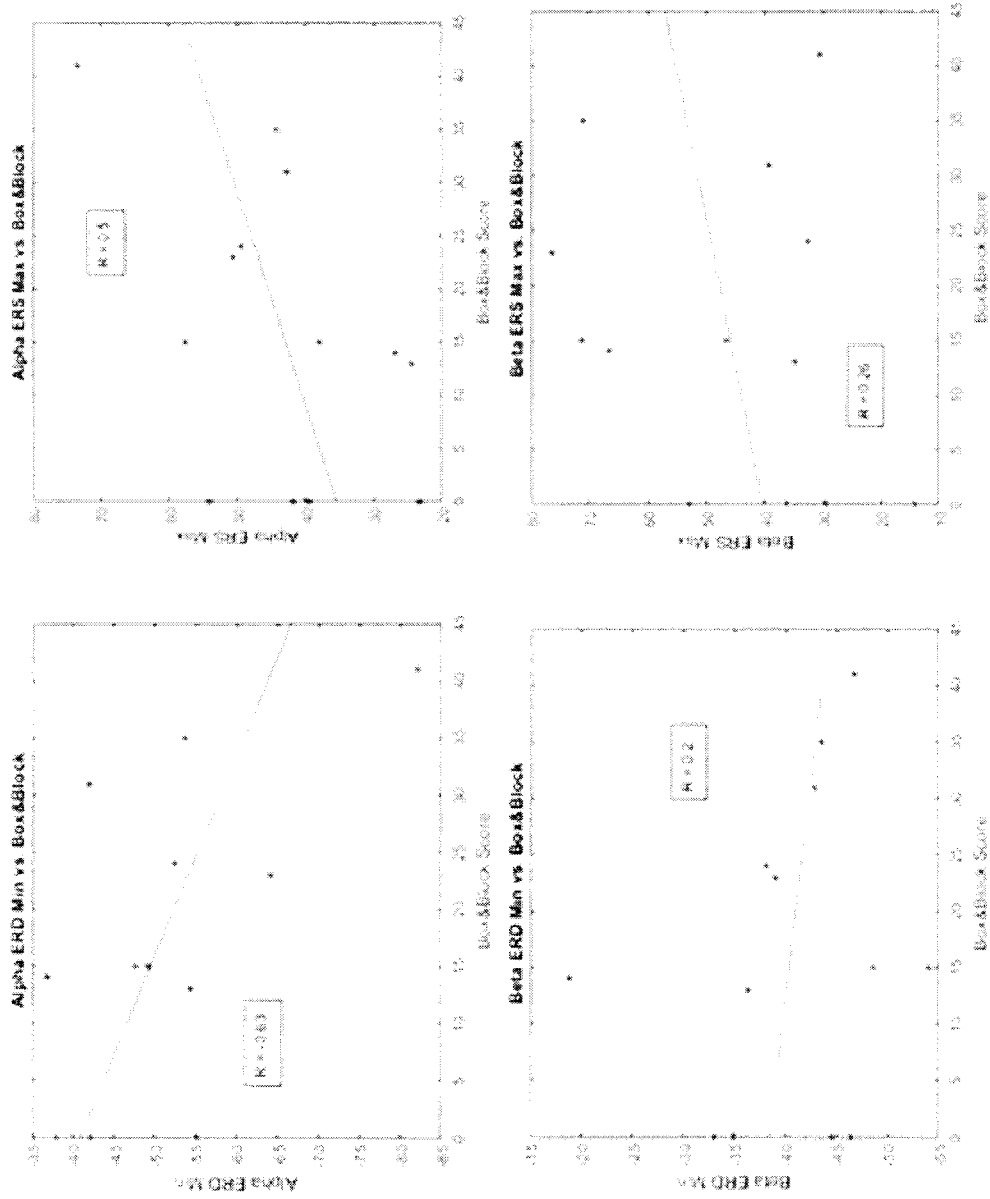
FIG. 9 contains graphs of correlation between ERD and ERS waveform maxima and minima and clinical box and block test scores.

In general terms, the motor control score may be derived from a set of secondary features of any form, and may comprise a linear or non-linear combination of these features. For example, summation or multiplication of extracted ERD/ERS secondary features can be used as a motor control score. Possible secondary features can include, for example, the peak value and area under the curve (AUC). These secondary features may be suitable candidates for generating motor control scores as they can be used as indicators of mobility. For example, the suitability of these secondary features can be shown by examining the correlation between ERD/ERS AUC and Box and Block Test scores (i.e. a clinically assessed score) for patients with stroke, as shown in FIG. 8. The highest Pearson's correlation identified between the alpha ERD maximum and minimum values and Box and Block Test (r=−0.63), and between beta ERS AUC and Box and Block Test (r=0.78), are shown in FIG. 9.

Additional secondary features that can be extracted from EEG waveforms (including, but not limited to, ERD/ERS waveforms) may include, for example: minimum of negative-going peak; maximum of positive-going peak; area-under-curve (AUC) of negative- or positive-going peak; overall AUC (sum of negative and positive AUC); average value in specific time intervals; total length of line; latency of negative-going peak; latency of positive-going peak; latency of zero-crossings; slope at specific time points; maximum positive slope; maximum negative slope; second derivative at specific time points; coefficients of best-fit modelling as n-degree polynomial; features derived from convolution or cross-correlation with representative waveforms (such as group average waveforms); features derived from convolution or cross-correlation between waveforms (such as between brain hemispheres); features derived from convolution or cross-correlation with subsections of representative waveforms; features derived from auto-correlation of the signal; measures of distance (Euclidean distance, sum of absolute point-to-point difference, etc.) from representative waveforms (such as group average waveforms); measures of distance (Euclidean distance, sum of absolute point-to-point difference, etc.) between waveforms (such as between brain hemispheres); R-squared coefficients with respect to representative waveforms (such as group average waveforms); R-squared coefficients between waveforms (such as between brain hemispheres); R-squared coefficients for subsections of waveforms; features derived from frequency domain; features derived from time-frequency domain; estimated variance or signal noise (either on average or at specific time points); any measure of curve moments (such as skewness or kurtosis); and any other related or suitable features.

The motor control score calculation may include one of or any combination of the following operations: summation of feature values; subtraction of feature values; multiplication of feature values; division of feature values; scaling of feature values by a constant (such as a known or estimated correlation coefficient for that feature type with a desired motor control score output); normalization of feature values relative to a known population distribution; exponentiation of feature values (raising to the power of any positive or negative value); scaling or multiplication of feature values with function (such as a sine wave); transformation of feature values by a function (such as a sine or cosine function); or any other suitable feature.

In one example implementation, the motor control score may be derived using the following general formula:

$$MScore = c_1 \cdot (a_1 \cdot \text{feature}_1 - b_1) + \ldots + c_n \cdot (a_n \cdot \text{feature}_n - b_n)$$

where features 1 to n are secondary feature values for specific ERD/ERS properties (e.g. minimum of alpha ERD peak, area-under-curve of beta ERS peak, etc.), where coefficients a and b are normalization factors which equalize all features into an approximate range from 0 to 100 with a mean value of 50, and where coefficients c are scaling factors which express relative importance of features or confidence in features or expected strength of feature correlation with motor activity. In this case, the scale and range of motor control score values would represent general motor function and can be arbitrarily normalized from 0 to 100. In other cases, where the motor control score is derived to specifically predict the results of existing clinical assessments (such as Fugl-Meyer assessment for individuals with stroke), the range of values can be adjusted to match that of the intended output prediction (e.g. 0 to 66 for upper limb Fugl-Meyer).

In another embodiment, the application of ERD/ERS features found in EEG data to quantify motor function can be implemented in the context of one or more artificial neural network models. Such models can be trained to generate clinically used motor function scores using EEG data as inputs into the model. The development of a suitable neural network model and application of the neural network model to motor function scores are described below.

In other embodiments, determination of motor control scores can be made by inputting ERD/ERS features or other processed EEG features into a deep neural network (DNN), either exclusively or in combination with raw/unprocessed EEG data. Special cases of DNN implementations are disclosed by Xia et al. "Electrooculogram based sleep stage classification using deep belief network", 2015 International Joint Conference on Neural Networks (IJCNN) 2015 Jul. 12 (pp. 1-5) (IEEE) and Mikolov et al. "Recurrent neural network based language model" in *INTERSPEECH*-2010, pp. 1045-1048.

Figure 10:
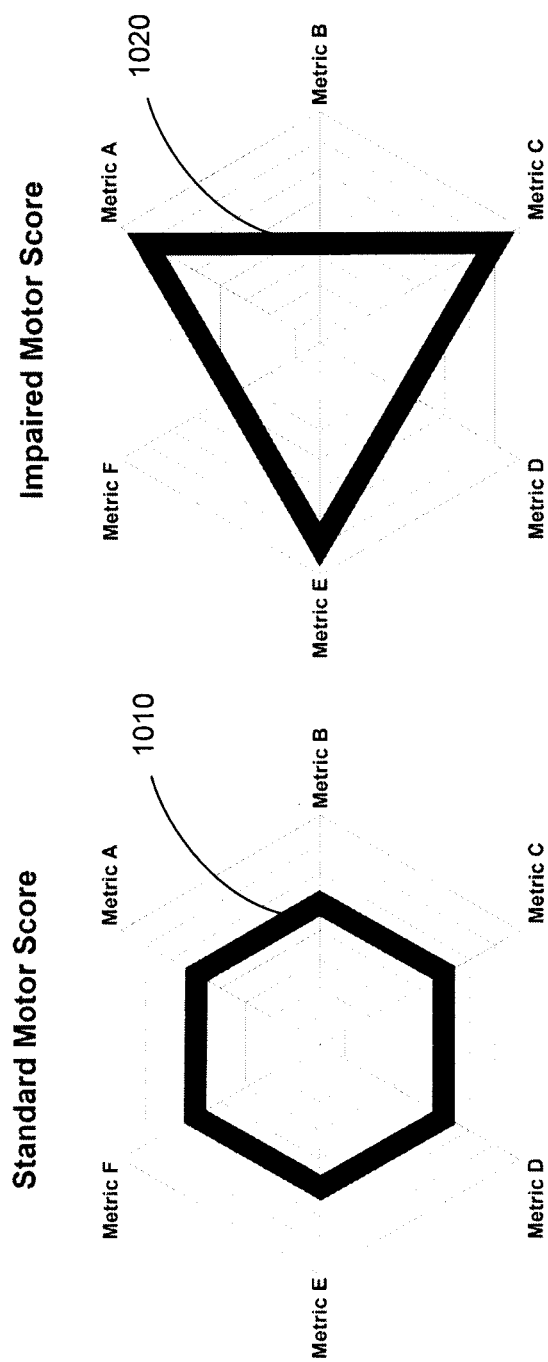
FIG. 10 is a representative visualization of a motor control score.

In certain embodiments, multiple output measures (e.g., if the DNN is trained to match multiple motor function measures) as the basis of the motor control score determination are considered. The output measures may be arranged geometrically such that the motor control score is represented as a shape (e.g., a hexagon for normal motor function and a triangle for impairment, as seen in FIG. 10). FIG. 10 shows the variation between a standard motor score 1010 and impaired motor score 1020 according to a hypothetical scenario. Combinations of function measures to be predicted may include: response time, dexterity, position accuracy, Fugl-Meyer score; right arm, left arm, right leg, left leg, head, and trunk; gross movements, fine movements; and a subgroup or a combination of the above.

In another embodiment, the motor control score can be determined using data fusion of brain activity signals with other biosignals such as electromyography (EMG). Specifically, EMG signals recorded from various muscle groups of the subject's body could be used, either as raw signals or after being filtered, as features for the DNN for calculating the motor control score.

Artificial Neural Network Implementation

In some cases, it may be desirable to use the motor control score to predict the results of existing clinical assessments (such as Fugl-Meyer assessment for individuals with stroke). In one exemplary implementation, an artificial neural network is implemented to use motor control scores to predict the results of existing clinical assessments. In this implementation, the inventors generated the necessary primary neural network models with EEG data acquired from 12 healthy participants and 14 participants with chronic stroke. The EEG data obtained from the participants may be processed using one or more steps of the above-described method 400 or another suitable processing method to provide the artificial neural network with suitable input data. In one embodiment, clicking events (i.e. benchmark movements) of the participants were time-stamped during the data acquisition. In another embodiment, additional rest periods were time-stamped during data acquisition. The collected EEG data is filtered using a 1-45 bandpass finite impulse response ("FIR") filter. Following filtration, the EEG data is separated into windows from 6 seconds before the clicking until 4 seconds after the clicking (e.g., based on the time-stamps). Fast Fourier transform is applied to the EEG data to extract the data's corresponding magnitude response and the phase response accordingly.

Figure 11:
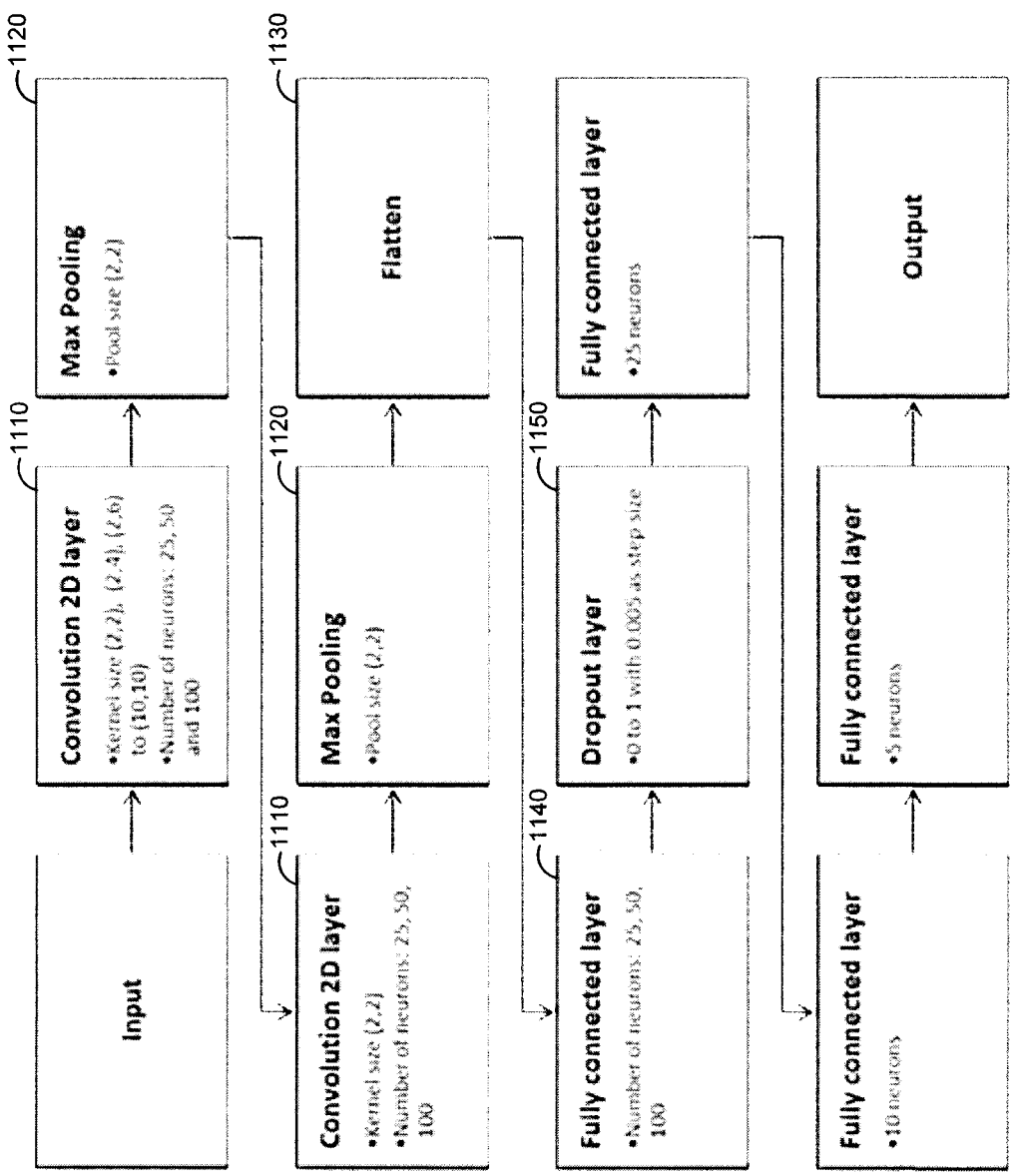
FIG. 11 is a flow chart for configuring a neural network model according to one implementation.

The artificial neural network models were generated with regression of the calculated motor control scores on the corresponding Fugl-Meyer Assessment (FMA) scores determined for each of the participants by way of traditional assessment on the day of the EEG scan. An exemplary neural network model configuration is shown in FIG. 11. Participant data in the form of power spectrum density and phase information of the EEG signal (i.e. signal and frequency components of the EEG data in each EEG waveform windows, including frequency elements in at least the alpha and beta bands) are used as input to the model configuration flow. In the example neural network model of FIG. 11, a two-dimensional convolutional neural network layer ("Convolution 2D layer" 1110), which calculates the convolution of adjacent elements in the input matrix with the designated kernel size and produces outputs with dimension as predefined in number of neurons. A "Max Pooling" layer 1120 is designed to take the maximum value from a designated submatrix from the output of the previous layer. In this example, the submatrix is in the form of 2×2 matrix. A "Flatten" layer 1130 in the example refers to reshaping of the output of the previous layer into a one-dimensional vector. A "Fully connected layer" 1140 refers to a network in which all the neural nodes are non-convolutional and fully connected. Such layer produces outputs with dimensions as predefined in number of neurons. A "Dropout layer" 1150 in the example includes special layers that randomly set a portion of outputs of the previous layer to zero. In the example configuration, the portion is searched from 0 to 1 with step size of 0.005. In the present model configuration, 30 trials of each participant's data were used in the model generation. All of the data was randomized and divided into batches of 16 trials to feed into the model training process. In the present implementation, overall, the acquired data was provided into the model generation framework for 200 repetitions.

Figure 12:
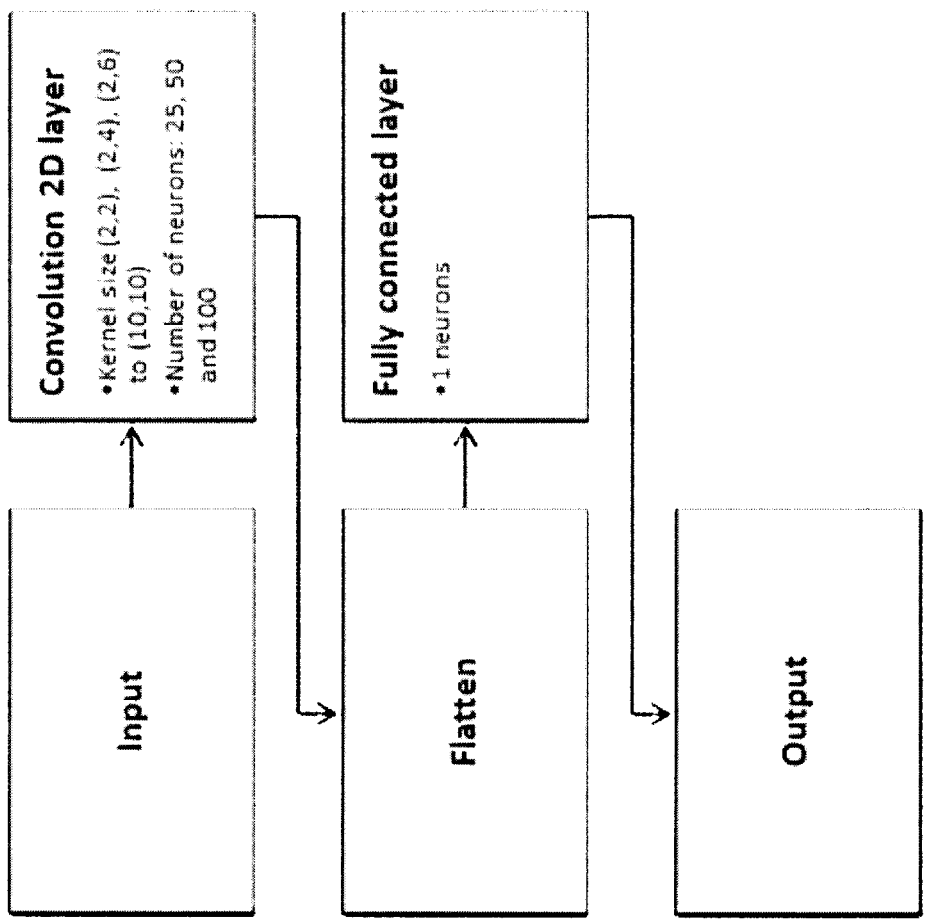
FIG. 12 is a flow chart for configuring a neural network model according to another implementation.

In another exemplary embodiment, a shallow neural network configuration may be used, as shown in FIG. 12. The shallow network contains fewer layers in its configuration as compared to the network model of FIG. 11. Therefore, the shallow network requires less data to train and is generally more computationally efficient. Such a neural network could better facilitate applications of the system that are deployed on mobile or portable computing devices.

The generated model is tested (validated) using data from participants that has not been used in the model training/generation process. This data, which contains the signal and frequency components such as frequency elements within at least the alpha and band bands, is provided to the model to test its ability to predict motor function scores. The result is summarized using within-participant test result and cross-participant test result, as described in more detail below.

For the within-participant test result, 30 trials' worth of EEG data from all participants during clicking was used in the model training. The remaining data, which was not involved in the model training/generation, is used in the model testing. In this case, only a part of the test participants' data has been exposed to the model in the model generation process. This scenario is analogous to acquiring a new EEG scan from the same participant to show the stability of the model performance.

For the cross-participant test, the EEG data of one participant is excluded from the training dataset. The model is generated with the 30 trials' worth of EEG data of the remaining participants. The model is tested with EEG data of a "brand new" participant (i.e. the excluded participant) that the model has never encountered in the training. This test scenario is analogous to predicting motor function performance of a new participant based on an existing dataset wherein the dataset does not include any data of the new participant.

Figure 13:
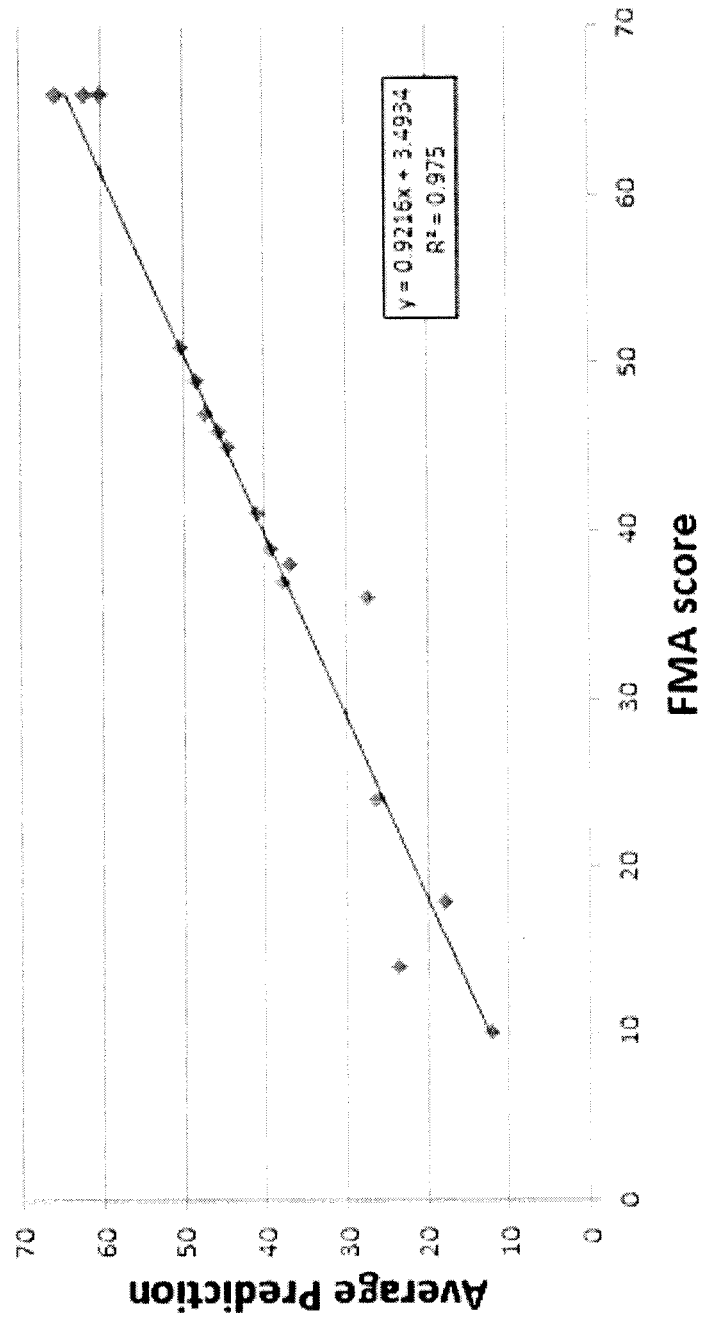
FIG. 13 is a graph showing the correlation of predicted Fugl-Myer Assessment (FMA) scores against measured FMA scores for a within-participant test.

In the above-described test scenarios, the neural network model is trained to predict FMA scores. The prediction of and the corresponding FMA score of the participant are interpolated as shown in FIG. 13 for the within-participant testing with a correlation coefficient $R^2$ value of 0.975. Based on the correlation result, it can be concluded that the neural network model converged well during training. In this model testing process, 30 trials' worth of EEG data of each participant during clicking were used in the model training. The remaining data was used in the model testing. Given a correlation coefficient value close to 1, high prediction accuracy is achievable in this artificial neural network approach with a within-participant test.

Figure 14:
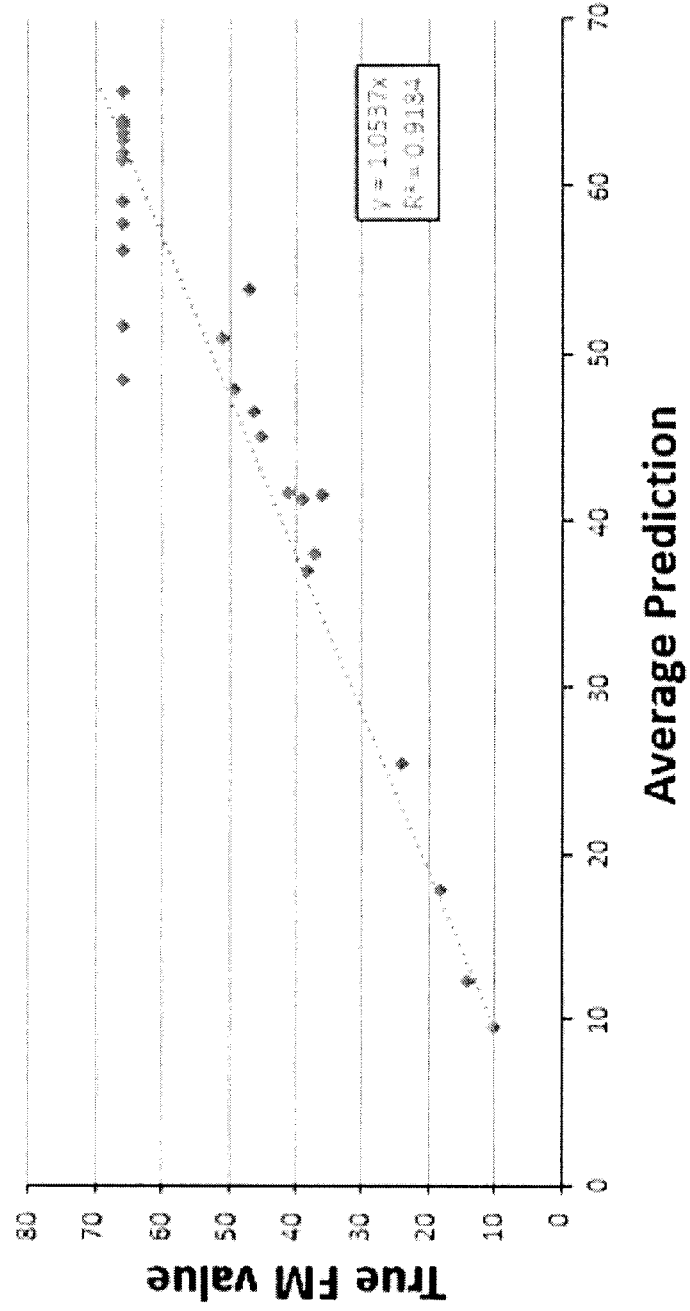
FIG. 14 is a graph showing the correlation of predicted Fugl-Myer Assessment (FMA) scores against measured FMA scores for a cross-participant test.

The inventors also conducted a cross-participant test of the artificial neural network by taking one participant out of the training process and training the neural network model using the remaining participants' EEG data. The excluded participant's EEG data is used in the model testing process. The testing results are summarized in FIG. 14 which shows a plot of average predicted FMA scores to actual FMA scores. For this particular study, a correlation coefficient $r=0.9583$ and a $R^2$ value of 0.9184 are obtainable, indicating a high level of correlation between predicted and actual scores. The performance of this model could be further improved with training EEG data from a larger population of participants and applying hyperparameter optimizing during training.

While the foregoing regression study makes use of FMA scores, it would be understood that regression assessments that are more responsive to motor function changes, such as for example the Wolf Motor Function Test (WFMT), can also be used.

In another embodiment, further analysis of the obtained artificial neural network models is used to assist with the interpretation of the effect of rehabilitation training or therapy on brain activation. The analysis includes, but is not limited to, using activation-maximization or another suitable method to visualize or analyze the features of the artificial neural network. While the output of the artificial neural network may indicate that the motor abilities of an individual are not changing over therapy, the analysis of the model can be used to understand if brain reorganization is occurring. This would, for instance, be the case if, over time, the artificial neural network selects different EEG features (either ERD/ERS or other activities in the EEG signals) to create the model.

Figure 15:
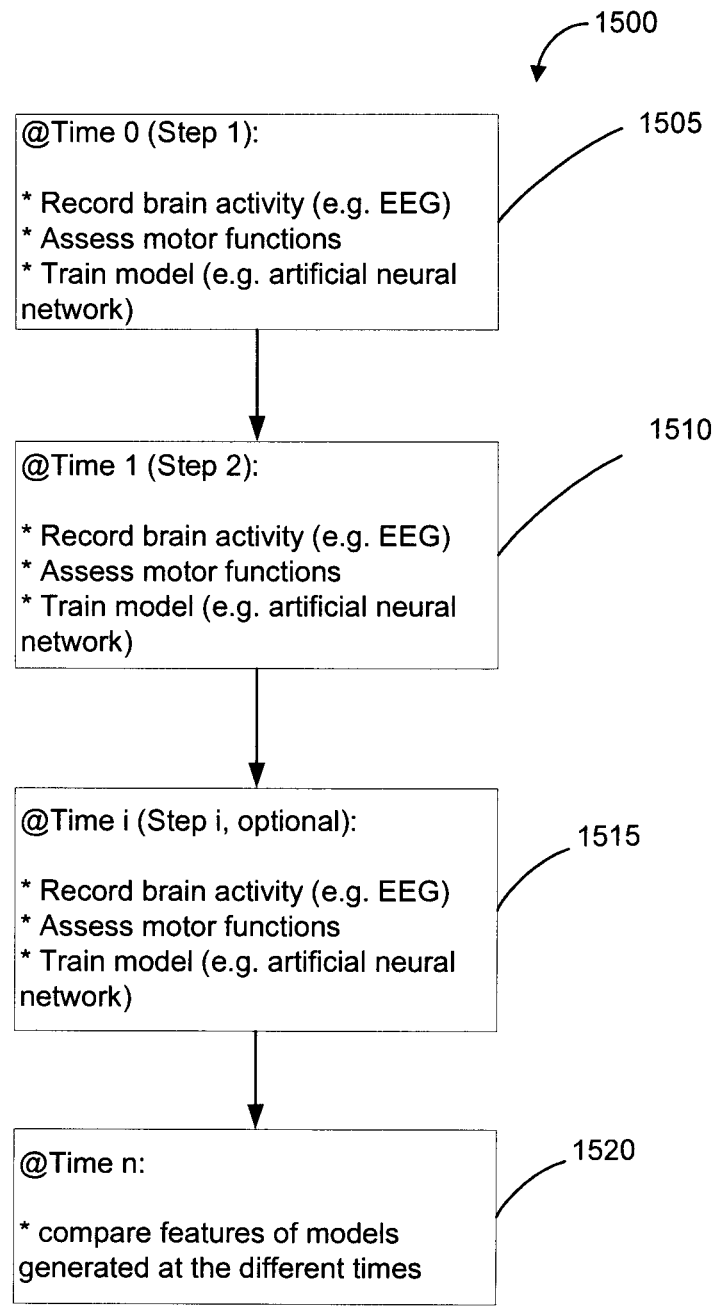
FIG. 15 is a flowchart for a method implementing activation-maximization to interpret the effect of rehabilitation training or therapy on brain activation.

FIG. 15 is a flowchart for method 1500 illustrating one possible application of artificial neural network model analysis to interpret the effect of rehabilitation training or therapy on brain activation. The method begins at step 1505, or "step 1", which involves a number of sub-steps including recording brain activity (e.g. using EEG), and assessing a subject's motor function (e.g. assessed either manually or using the mobility assessment system 100 disclosed herein), and training a mathematical model such as an artificial neural network using the recorded brain activity and corresponding motor function. The method of step one can be said to take place at a time with time reference name "time 0" (zero).

Next, at step 1510, or "step 2", the sub-steps of step 1 are repeated, but at a different time. The frequency of the assessments may vary depending on the applications and purposes. For example, the frequency may be daily, weekly or monthly. More specifically, the time during which step one is repeated can be said to take place at a time with time reference name "time 1".

Step 1515, or "step i", is an optional step in which step 1 may be repeated multiple times (each repetition being an instance of step i) so that multiple mathematical models are generated.

At step 1520, or "step n", the method requires comparing the parameters of the mathematical models generated using the brain activity data and motor function scores. The comparison could be done with element-by-element method or other analysis using visualization methods such as activation maximization to understand if brain montage has changed.

The examples and corresponding diagrams used herein are for illustrative purposes only. Different configurations and terminology can be used without departing from the principles expressed herein.

Although the invention has been described with reference to certain specific embodiments, various modifications thereof will be apparent to those skilled in the art without departing from the scope of the invention. The scope of the claims should not be limited by the illustrative embodiments set forth in the examples, but should be given the broadest interpretation consistent with the description as a whole.

The invention claimed is:

1. A computer-implemented method to automatically generate a motor control score for a subject based on electroencephalography (EEG) data represented as a plurality of EEG waveforms obtained from a plurality of EEG electrodes, the method comprising:
   (a) for each EEG waveform of the plurality of EEG waveforms, separating the EEG waveform into at least one window, wherein each window contains a portion of the EEG waveform representative of neural activity corresponding to a movement performed by the subject;
   (b) determining, from the EEG data in the at least one window, at least one or more frequency components; and
   (c) calculating the motor control score based on the at least one or more frequency components, wherein
   the one or more frequency components correspond to at least one phase response of the at least one window;
   at least one or more signal components are determined from the EEG data in the at least one window, the one or more signal components corresponding to at least one signal power spectrum density of the at least one window; and
   the motor control score is calculated using a primary neural network, the primary neural network being provided with the EEG data in the at least one window as input comprising the at least one phase response and the at least one signal power spectrum density.

2. The computer-implemented method of claim 1, wherein the plurality of EEG waveforms are filtered using a 1 Hz to 45 Hz bandpass finite impulse response filter prior to the step of separating the EEG waveforms into the at least one window.

3. The computer-implemented method of claim 1, wherein the phase response of the EEG data in the at least one window comprises elements within at least one of an alpha band and a beta band.

4. The computer-implemented method of claim 1, wherein fast Fourier transform is performed on the at least one window to obtain the at least one phase response and the at least one signal power spectrum density.

5. The computer-implemented method of claim 1, wherein the primary neural network is configured using regression with a training data set having training phase responses and training power spectrum densities in a plurality of training EEG waveforms, and a plurality of manually-assessed clinical motor function scores associated with the plurality of training EEG waveforms.

6. The computer-implemented method of claim 1, wherein the at least one phase response and the at least one signal power spectrum density is calculated from a corresponding frequency domain representation of the at least one window.

7. The computer-implemented method of claim 1, wherein the primary neural network model is configured using a configuration framework comprising at least two two-dimensional convolutional neural network layers, at least two max pooling layers, and at least two fully connected layers.

8. The computer-implemented method of claim 1, wherein the primary neural network model is configured using a configuration framework comprising a two-dimensional convolutional neural network layer and a fully connected layer.

\* \* \* \* \*